US008348978B2

(12) United States Patent
Trieu et al.

(10) Patent No.: US 8,348,978 B2
(45) Date of Patent: Jan. 8, 2013

(54) INTEROSTEOTIC IMPLANT

(75) Inventors: Hai H. Trieu, Cordova, TN (US);
Thomas Carls, Memphis, TN (US); Roy Lim, Memphis, TN (US); Eric C. Lange, Collierville, TN (US); Kent M. Anderson, Memphis, TN (US); Aurelien Bruneau, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1768 days.

(21) Appl. No.: 11/413,785

(22) Filed: Apr. 28, 2006

(65) Prior Publication Data
US 2007/0270826 A1  Nov. 22, 2007

(51) Int. Cl.
*A61B 17/70* (2006.01)
(52) U.S. Cl. ........................................ 606/278; 606/279
(58) Field of Classification Search .... 623/17.11–17.16; 606/94, 247, 248, 249, 278, 279
See application file for complete search history.

(56) References Cited

U.S. PATENT DOCUMENTS

| | | |
|---|---|---|
| 2,677,369 A | 5/1954 | Knowles |
| 3,648,691 A | 3/1972 | Lumb et al. |
| 3,867,728 A | 2/1975 | Stubstad et al. |
| 4,003,376 A | 1/1977 | McKay et al. |
| 4,011,602 A | 3/1977 | Rybicki et al. |
| 4,078,559 A | 3/1978 | Nissinen |
| 4,257,409 A | 3/1981 | Bacal et al. |
| 4,554,914 A | 11/1985 | Kapp et al. |
| 4,570,618 A | 2/1986 | Wu |
| 4,573,454 A | 3/1986 | Hoffman |
| 4,604,995 A | 8/1986 | Stephens et al. |
| 4,643,178 A | 2/1987 | Nastari et al. |
| 4,686,970 A | 8/1987 | Dove et al. |
| 4,827,918 A | 5/1989 | Olerud |
| 4,936,848 A | 6/1990 | Bagby |
| 4,969,888 A | 11/1990 | Scholten et al. |
| 5,011,484 A | 4/1991 | Breard |
| 5,047,055 A | 9/1991 | Bao et al. |
| 5,092,866 A | 3/1992 | Breard et al. |
| 5,171,280 A | 12/1992 | Baumgartner |
| 5,192,326 A * | 3/1993 | Bao et al. .................... 623/17.12 |
| 5,201,734 A | 4/1993 | Cozad et al. |
| 5,236,460 A | 8/1993 | Barber |
| 5,242,444 A | 9/1993 | MacMillan |
| 5,306,275 A | 4/1994 | Bryan |
| 5,314,477 A | 5/1994 | Marnay |
| 5,360,430 A | 11/1994 | Lin |
| 5,366,455 A | 11/1994 | Dove |
| 5,415,661 A | 5/1995 | Holmes |

(Continued)

FOREIGN PATENT DOCUMENTS

DE         2821678 A1     11/1979
(Continued)

OTHER PUBLICATIONS

U.S. Appl. No. 11/442,621, filed May 26, 2006, Allard et al.

(Continued)

*Primary Examiner* — Pedro Philogene

(57) ABSTRACT

An implant is disclosed and can include a body and a plurality of pellets disposed within the body. The implant can be moved between an unmolded, relaxed configuration wherein the body is not conformed to a bone and a molded, relaxed configuration wherein the body is at least partially conformed to the bone.

8 Claims, 18 Drawing Sheets

U.S. PATENT DOCUMENTS

| | | | |
|---|---|---|---|
| 5,437,672 A | 8/1995 | Alleyne | |
| 5,454,812 A | 10/1995 | Lin | |
| 5,496,318 A | 3/1996 | Howland et al. | |
| 5,527,312 A | 6/1996 | Ray | |
| 5,549,679 A | 8/1996 | Kuslich | |
| 5,571,189 A | 11/1996 | Kuslich | |
| 5,609,634 A | 3/1997 | Voydeville | |
| 5,628,756 A | 5/1997 | Barker, Jr. et al. | |
| 5,645,597 A | 7/1997 | Krapiva | |
| 5,645,599 A | 7/1997 | Samani | |
| 5,665,122 A | 9/1997 | Kambin | |
| 5,674,295 A | 10/1997 | Ray et al. | |
| 5,676,702 A | 10/1997 | Ratron | |
| 5,690,649 A | 11/1997 | Li | |
| 5,702,452 A | 12/1997 | Argenson et al. | |
| 5,725,582 A | 3/1998 | Bevan et al. | |
| 5,746,762 A | 5/1998 | Bass | |
| 5,755,797 A * | 5/1998 | Baumgartner | 623/17.16 |
| 5,810,815 A | 9/1998 | Morales | |
| 5,836,948 A | 11/1998 | Zucherman et al. | |
| 5,860,977 A | 1/1999 | Zucherman et al. | |
| 5,976,186 A | 11/1999 | Bao et al. | |
| 6,019,792 A | 2/2000 | Cauthen | |
| 6,022,376 A | 2/2000 | Assell et al. | |
| 6,048,342 A | 4/2000 | Zucherman et al. | |
| 6,066,154 A | 5/2000 | Reiley et al. | |
| 6,068,630 A | 5/2000 | Zucherman et al. | |
| 6,099,565 A * | 8/2000 | Sakura, Jr. | 623/8 |
| 6,132,464 A | 10/2000 | Martin | |
| 6,179,874 B1 | 1/2001 | Cauthen | |
| 6,187,043 B1 * | 2/2001 | Ledergerber | 623/8 |
| 6,238,397 B1 | 5/2001 | Zucherman et al. | |
| 6,277,120 B1 | 8/2001 | Lawson | |
| 6,293,949 B1 | 9/2001 | Justis et al. | |
| 6,299,613 B1 | 10/2001 | Ogilvie et al. | |
| 6,332,894 B1 | 12/2001 | Stalcup et al. | |
| 6,336,930 B1 | 1/2002 | Stalcup et al. | |
| 6,352,537 B1 | 3/2002 | Strnad | |
| 6,364,883 B1 | 4/2002 | Santilli | |
| 6,395,034 B1 | 5/2002 | Suddaby | |
| 6,402,750 B1 | 6/2002 | Atkinson et al. | |
| 6,402,785 B1 | 6/2002 | Zdeblick et al. | |
| 6,419,704 B1 | 7/2002 | Ferree | |
| 6,425,923 B1 | 7/2002 | Stalcup et al. | |
| 6,440,168 B1 | 8/2002 | Cauthen | |
| 6,440,169 B1 | 8/2002 | Elberg et al. | |
| 6,447,514 B1 | 9/2002 | Stalcup et al. | |
| 6,451,019 B1 | 9/2002 | Zucherman et al. | |
| 6,558,390 B2 | 5/2003 | Cragg | |
| 6,582,433 B2 | 6/2003 | Yun | |
| 6,626,944 B1 | 9/2003 | Taylor | |
| 6,645,207 B2 | 11/2003 | Dixon et al. | |
| 6,645,248 B2 | 11/2003 | Casutt | |
| 6,695,842 B2 | 2/2004 | Zucherman et al. | |
| 6,709,435 B2 | 3/2004 | Lin | |
| 6,723,126 B1 | 4/2004 | Berry | |
| 6,733,534 B2 * | 5/2004 | Sherman | 623/17.16 |
| 6,761,720 B1 | 7/2004 | Senegas | |
| 6,805,697 B1 | 10/2004 | Helm et al. | |
| 6,835,205 B2 | 12/2004 | Atkinson et al. | |
| 6,852,128 B2 | 2/2005 | Lange | |
| 6,863,688 B2 | 3/2005 | Ralph et al. | |
| 6,899,713 B2 | 5/2005 | Shaolian et al. | |
| 6,946,000 B2 | 9/2005 | Senegas et al. | |
| 6,958,077 B2 | 10/2005 | Suddaby | |
| 6,969,404 B2 | 11/2005 | Ferree | |
| 6,969,405 B2 | 11/2005 | Suddaby | |
| 6,972,036 B2 | 12/2005 | Boehm, Jr. et al. | |
| 7,041,136 B2 | 5/2006 | Goble et al. | |
| 7,048,736 B2 | 5/2006 | Robinson et al. | |
| 7,081,120 B2 | 7/2006 | Li et al. | |
| 7,087,083 B2 | 8/2006 | Pasquet et al. | |
| 7,105,024 B2 | 9/2006 | Richelsoph | |
| 7,163,558 B2 | 1/2007 | Senegas et al. | |
| 7,201,751 B2 | 4/2007 | Zucherman et al. | |
| 7,238,204 B2 | 7/2007 | Le Couedic et al. | |
| 7,306,628 B2 | 12/2007 | Zucherman et al. | |
| 7,377,942 B2 | 5/2008 | Berry | |
| 7,442,208 B2 | 10/2008 | Mathieu et al. | |
| 7,445,637 B2 | 11/2008 | Taylor | |
| 2002/0029039 A1 | 3/2002 | Zucherman et al. | |
| 2002/0133155 A1 | 9/2002 | Ferree | |
| 2002/0143331 A1 | 10/2002 | Zucherman et al. | |
| 2003/0040746 A1 | 2/2003 | Mitchell et al. | |
| 2003/0139814 A1 | 7/2003 | Bryan | |
| 2003/0153915 A1 | 8/2003 | Nekozuka et al. | |
| 2003/0220649 A1 | 11/2003 | Bao et al. | |
| 2004/0055607 A1 | 3/2004 | Boehm, Jr. et al. | |
| 2004/0083002 A1 | 4/2004 | Belef et al. | |
| 2004/0097931 A1 | 5/2004 | Mitchell | |
| 2004/0186475 A1 | 9/2004 | Falahee | |
| 2004/0186576 A1 | 9/2004 | Biscup et al. | |
| 2004/0215342 A1 | 10/2004 | Suddaby | |
| 2004/0225360 A1 | 11/2004 | Malone | |
| 2004/0230305 A1 | 11/2004 | Gorensek et al. | |
| 2004/0267368 A1 * | 12/2004 | Kuslich | 623/17.16 |
| 2005/0010293 A1 | 1/2005 | Zucherman et al. | |
| 2005/0033431 A1 | 2/2005 | Gordon et al. | |
| 2005/0033432 A1 | 2/2005 | Gordon et al. | |
| 2005/0033437 A1 | 2/2005 | Bao et al. | |
| 2005/0033439 A1 | 2/2005 | Gordon et al. | |
| 2005/0038432 A1 | 2/2005 | Shaolian et al. | |
| 2005/0049708 A1 | 3/2005 | Atkinson et al. | |
| 2005/0101955 A1 | 5/2005 | Zucherman et al. | |
| 2005/0143738 A1 | 6/2005 | Zucherman et al. | |
| 2005/0165398 A1 | 7/2005 | Reiley | |
| 2005/0197702 A1 | 9/2005 | Coppes et al. | |
| 2005/0203512 A1 | 9/2005 | Hawkins et al. | |
| 2005/0203624 A1 | 9/2005 | Serhan et al. | |
| 2005/0203626 A1 | 9/2005 | Sears et al. | |
| 2005/0209696 A1 | 9/2005 | Lin et al. | |
| 2005/0216017 A1 | 9/2005 | Fielding et al. | |
| 2005/0228391 A1 | 10/2005 | Levy et al. | |
| 2005/0240267 A1 | 10/2005 | Randall et al. | |
| 2005/0261768 A1 | 11/2005 | Trieu | |
| 2005/0267580 A1 | 12/2005 | Suddaby | |
| 2005/0273110 A1 | 12/2005 | Boehm, Jr. et al. | |
| 2005/0288672 A1 | 12/2005 | Ferree | |
| 2006/0004367 A1 | 1/2006 | Alamin et al. | |
| 2006/0004447 A1 | 1/2006 | Mastrorio et al. | |
| 2006/0015181 A1 | 1/2006 | Elberg | |
| 2006/0015183 A1 | 1/2006 | Gilbert et al. | |
| 2006/0036246 A1 | 2/2006 | Carl et al. | |
| 2006/0036256 A1 | 2/2006 | Carl et al. | |
| 2006/0036259 A1 | 2/2006 | Carl et al. | |
| 2006/0036323 A1 | 2/2006 | Carl et al. | |
| 2006/0036324 A1 | 2/2006 | Sachs et al. | |
| 2006/0058790 A1 | 3/2006 | Carl et al. | |
| 2006/0064165 A1 | 3/2006 | Zucherman et al. | |
| 2006/0084983 A1 | 4/2006 | Kim | |
| 2006/0084985 A1 | 4/2006 | Kim | |
| 2006/0084987 A1 | 4/2006 | Kim | |
| 2006/0084988 A1 | 4/2006 | Kim | |
| 2006/0085069 A1 | 4/2006 | Kim | |
| 2006/0085070 A1 | 4/2006 | Kim | |
| 2006/0085074 A1 | 4/2006 | Raiszadeh | |
| 2006/0089654 A1 | 4/2006 | Lins et al. | |
| 2006/0089719 A1 | 4/2006 | Trieu | |
| 2006/0106381 A1 | 5/2006 | Ferree et al. | |
| 2006/0106397 A1 | 5/2006 | Lins | |
| 2006/0111728 A1 | 5/2006 | Abdou | |
| 2006/0122620 A1 | 6/2006 | Kim | |
| 2006/0136060 A1 | 6/2006 | Taylor | |
| 2006/0184247 A1 | 8/2006 | Edidin et al. | |
| 2006/0184248 A1 | 8/2006 | Edidin et al. | |
| 2006/0195102 A1 | 8/2006 | Malandain | |
| 2006/0217726 A1 | 9/2006 | Maxy et al. | |
| 2006/0235387 A1 | 10/2006 | Peterman | |
| 2006/0235532 A1 | 10/2006 | Meunier et al. | |
| 2006/0241613 A1 | 10/2006 | Brueneau et al. | |
| 2006/0247623 A1 | 11/2006 | Anderson et al. | |
| 2006/0247640 A1 | 11/2006 | Blackwell et al. | |
| 2006/0253198 A1 * | 11/2006 | Myint et al. | 623/17.12 |
| 2006/0264938 A1 | 11/2006 | Zucherman et al. | |
| 2006/0271044 A1 | 11/2006 | Petrini et al. | |
| 2006/0293662 A1 | 12/2006 | Boyer, II et al. | |
| 2006/0293663 A1 | 12/2006 | Walkenhorst et al. | |

| | | | |
|---|---|---|---|
| 2007/0043362 A1 | 2/2007 | Malandain et al. | |
| 2007/0073292 A1* | 3/2007 | Kohm et al. | 606/61 |
| 2007/0088436 A1 | 4/2007 | Parsons et al. | |
| 2007/0162000 A1 | 7/2007 | Perkins | |
| 2007/0198091 A1 | 8/2007 | Boyer et al. | |
| 2007/0233068 A1 | 10/2007 | Bruneau et al. | |
| 2007/0233081 A1 | 10/2007 | Pasquet et al. | |
| 2007/0233089 A1 | 10/2007 | DiPoto et al. | |
| 2007/0233146 A1* | 10/2007 | Henniges et al. | 606/91 |
| 2007/0270834 A1 | 11/2007 | Bruneau et al. | |
| 2008/0161818 A1 | 7/2008 | Kloss et al. | |

FOREIGN PATENT DOCUMENTS

| | | |
|---|---|---|
| DE | 101 49 385 A1 | 4/2003 |
| EP | 0418387 A1 | 3/1991 |
| EP | 0322334 B1 | 2/1992 |
| EP | 0 661 957 B1 | 9/1998 |
| EP | 1138268 A1 | 10/2001 |
| EP | 1330987 A1 | 7/2003 |
| FR | 2623085 A1 | 5/1989 |
| FR | 2625097 A1 | 6/1989 |
| FR | 2681525 A | 3/1993 |
| FR | 2681525 A1 | 3/1993 |
| FR | 2700941 A1 | 8/1994 |
| FR | 2703239 A1 | 10/1994 |
| FR | 2707864 A1 | 1/1995 |
| FR | 2717675 A1 | 9/1995 |
| FR | 2722087 A | 1/1996 |
| FR | 2722087 A1 | 1/1996 |
| FR | 2722088 A1 | 1/1996 |
| FR | 2724554 A1 | 3/1996 |
| FR | 2725892 A1 | 4/1996 |
| FR | 2730156 A1 | 8/1996 |
| FR | 2775183 A1 | 8/1999 |
| FR | 2799640 A | 4/2001 |
| FR | 2799948 A1 | 4/2001 |
| FR | 2816197 A1 | 5/2002 |
| FR | 2851154 A | 8/2004 |
| JP | 02-224660 | 9/1990 |
| JP | 09-075381 | 3/1997 |
| SU | 988281 | 1/1983 |
| SU | 1484348 A1 | 6/1989 |
| WO | WO 91/13598 | 9/1991 |
| WO | WO 94/26192 | 11/1994 |
| WO | WO 94/26195 | 11/1994 |
| WO | WO 98/20939 | 5/1998 |
| WO | WO 98/34568 | 8/1998 |
| WO | WO 99/59669 | 11/1999 |
| WO | WO 00/45752 | 8/2000 |
| WO | WO 01/15638 A1 | 3/2001 |
| WO | WO 02/09625 A1 | 2/2002 |
| WO | WO 03/007829 | 1/2003 |
| WO | WO 2004/028401 A2 | 4/2004 |
| WO | WO 2004/047691 A1 | 6/2004 |
| WO | 2004/084768 A | 10/2004 |
| WO | WO 2004/084768 A2 | 10/2004 |
| WO | 2005/002474 A | 1/2005 |
| WO | WO 2005/002474 A1 | 1/2005 |
| WO | 2005/009300 A | 2/2005 |
| WO | WO 2005/009300 A1 | 2/2005 |
| WO | WO 2005/016194 A2 | 2/2005 |
| WO | WO 2005/044118 A1 | 5/2005 |
| WO | WO 2005/097004 A2 | 10/2005 |
| WO | WO 2005/110258 A1 | 11/2005 |
| WO | WO 2005/115261 A1 | 12/2005 |
| WO | WO 2006/009855 A2 | 1/2006 |
| WO | 2006/025815 A | 3/2006 |
| WO | 2006/044786 A | 4/2006 |
| WO | WO 2006/064356 A1 | 6/2006 |
| WO | 2006/089085 A | 8/2006 |
| WO | WO 2007/034516 A1 | 3/2007 |
| WO | 2007/075788 A | 7/2007 |

OTHER PUBLICATIONS

U.S. Appl. No. 11/481,079, filed Jul. 5, 2006, Anderson et al.
"Dispositivo Intervertebrale Ammortizzante DIAM," date unknown, p. 1.
"Tecnica Operatoria Per Il Posizionamento Della Protesi DIAM," date unknown, pp. 1-3.
"Wallis Operative Technique: Surgical Procedure for Treatment of Degenerative Disc Disease (DDD) of Lumbar Spine," date unknown, pp. 1-24, Spine Next, an Abbott Laboratories company, Bordeaux, France.
Benzel et al., "Posterior Cervical Interspinous Compression Wiring and Fusion for Mid to Low Cervical Spinal Injuries," J. Neurosurg., Jun. 1989, pp. 893-899, vol. 70.
Caserta et al., "Elastic Stabilization Alone or Combined with Rigid Fusion in Spinal Surgery: a Biomechanical Study and Clinical Experience Based on 82 Cases," Eur. Spine J., Oct. 2002, pp. S192-S197, vol. 11, Suppl. 2.
Christie et al., "Dynamic Interspinous Process Technology," SPINE, 2005, pp. S73-S78, vol. 30, No. 16S.
Cousin Biotech, "Analysis of Clinical Experience with a Posterior Shock-Absorbing Implant," date unknown, pp. 2-9.
Cousin Biotech, Dispositif Intervertébral Amortissant, Jun. 1998, pp. 1-4.
Cousin Biotech, Technique Operatoire de la Prothese DIAM, date unknown, Annexe 1, pp. 1-8.
Dickman et al., "The Interspinous Method of Posterior Atlantoaxial Arthrodesis," J. Neurosurg., Feb. 1991, pp. 190-198, vol. 74.
Dubois et al., "Dynamic Neutralization: A New Concept for Restabilization of the Spine," Lumbar Segmental Insability, Szpalski et al., eds., 1999, pp. 233-240, Lippincott Williams & Wilkins, Philadelphia, Pennsylvania.
Duff, "Methyl Methacrylate in Spinal Stabilization," Techniques in Spinal Fusion and Stabilization, Hitchon et al., eds., 1995, pp. 147-151, Ch. 14, Thieme, New York.
Ebara et al., "Inoperative Measurement of Lumbar Spinal Instability," SPINE, 1992, pp. S44-S50, vol. 17, No. 3S.
Fassio et al., "Treatment of Degenerative Lumbar Spinal Instability L4-L5 by Interspinous Ligamentoplasty," Rachis, Dec. 1991, pp. 465-474, vol. 3, No. 6.
Fassio, "Mise au Point Sur la Ligamentoplastie Inter-Epineuse Lombaire Dans les Instabilites," Maîtrise Orthopédique, Jul. 1993, pp. 18, No. 25.
Garner et al., "Development and Preclinical Testing of a New Tension-Band Device for the Spine: the Loop System," Eur. Spine J., Aug. 7, 2002, pp. S186-S191, vol. 11, Suppl. 2.
Guang et al., "Interspinous Process Segmental Instrumentation with Bone-Button-Wire for Correction of Scoliosis," Chinese Medical J., 1990, pp. 721-725, vol. 103.
Guizzardi et al., "The Use of DIAM (Interspinous Stress-Breaker Device) in the Prevention of Chronic Low Back Pain in Young Patients Operated on for Large Dimension Lumbar Disc Herniation," 12th Eur. Cong. Neurosurg., Sep. 7-12, 2003, pp. 835-839, Port.
Hambly et al., "Tension Band Wiring-Bone Grafting for Spondylolysis and Spondylolisthesis," SPINE, 1989, pp. 455-460, vol. 14, No. 4.
Kiwerski, "Rehabilitation of Patients with Thoracic Spine Injury Treated by Spring Alloplasty," Int. J. Rehab. Research, 1983, pp. 469-474, vol. 6, No. 4.
Kramer et al., "Intevetertebral Disk Diseases: Causes, Diagnosis, Treatment and Prophylaxis," pp. 244-249, Medical, 1990.
Laudet et al., "Comportement Bio-Mécanique D'Un Ressort Inter-Apophysaire Vertébral Postérieur Analyse Expérimentale Due Comportement Discal En Compression Et En Flexion/Extension," Rachis, 1993, vol. 5, No. 2.
Mah et al., "Threaded K-Wire Spinous Process Fixation of the Axis for Modified Gallie Fusion in Children and Adolescents," J. Pediatric Othopaedics, 1989, pp. 675-679, vol. 9.
Mariottini et al., "Preliminary Results of a Soft Novel Lumbar Intervertebral Prothesis (DIAM) in the Degenerative Spinal Pathology," Acta Neurochir., Adv. Peripheral Nerve Surg. and Minimal Invas. Spinal Surg., 2005, pp. 129-131, vol. 92, Suppl.
McDonnell et al., "Posterior Atlantoaxial Fusion: Indications and Techniques," Techniques in Spinal Fusion and Stabilization, Hitchon et al., eds., 1995, pp. 92-106, Ch. 9, Thieme, New York.
Minns et al., "Preliminary Design and Experimental Studies of a Novel Soft Implant for Correcting Sagittal Plane Instability in the Lumbar Spine," SPINE, 1997, pp. 1819-1825, vol. 22, No. 16.

Müller, "Restauration Dynamique de la Stabilité Rachidienne," Tiré de la Sulzer Technical Review, Jan. 1999, Sulzer Management Ltd, Winterthur, Switzerland.

Pennal et al., "Stenosis of the Lumbar Spinal Canal," Clinical Neurosurgery: Proceedings of the Congress of Neurological Surgeons, St. Louis, Missouri, 1970, Tindall et al., eds., 1971, Ch. 6, pp. 86-105, vol. 18.

Petrini et al., "Analisi Di Un'Esperienza Clinica Con Un Impianto Posteriore Ammortizzante," S.O.T.I.M.I. Società di Ortopedia e Traumatologia dell'Italia Meridionale e Insulare 90° Congresso, Jun. 21-23, 2001, Paestum.

Petrini et al., "Stabilizzazione Elastica," Patologia Degenerativa del Rachide Lombare, Oct. 5-6, 2001, Rimini.

Porter, "Spinal Stenosis and Neurogenic Claudication," SPINE, Sep. 1, 1996, pp. 2046-2052, vol. 21, No. 17.

Pupin et al., "Clinical Experience with a Posterior Shock-Absorbing Implant in Lumbar Spine," World Spine 1: First Interdisciplinary World Congress on Spinal Surgery and Related Disciplines, Aug. 27-Sep. 1, 2000, Berlin, Germany.

Rengachary et al., "Cervical Spine Stabilization with Flexible, Multistrand Cable System," Techniques in Spinal Fusion and Stabilization, Hitchon et al., eds., 1995, pp. 79-81, Ch. 7, Thieme, New York.

Richards et al., "The Treatment Mechanism of an Interspinous Process Implant for Lumbar Neurogenic Intermittent Claudication," SPINE, 2005, pp. 744-749, vol. 30, No. 7.

Scarfò, "Instability/Stenosis: Holistic Approach for Less Invasive Surgery," date unknown, University of Siena, Siena, Italy.

Schiavone et al., "The Use of Disc Assistance Prosthesis (DIAM) in Degenerative Lumbar Pathology: Indications, Technique, Results," Italian J. Spinal Disorders, 2003, pp. 213-220, vol. 3, No. 2.

Schlegel et al., "The Role of Distraction in Improving the Space Available in the Lumbar Stenotic Canal and Foramen," SPINE, 1994, pp. 2041-2047, vol. 19, No. 18.

Senegas et al., "Le Recalibrage du Canal Lombaire, Alternative à la Laminectomie dans le Traitement des Sténoses du Canal Lombaire," Revue de Chirurgie Orthopédique, 1988, pp. 15-22.

Senegas et al., "Stabilisation Lombaire Souple," Instabilité Vertébrates Lombaires, Gastambide, ed., 1995, pp. 122-132, Expansion Scientifique Française, Paris, France.

Senegas, "La Ligamentoplastie Inter Vertébrale Lombaire, Alternative a L'Arthrodèse," La Revue de Medécine Orthopédique, Jun. 1990, pp. 33-35, No. 20.

Senegas, "La Ligamentoplastie Intervertébrale, Alternative à L'arthrodèse dans le Traitement des Instabilités Dégénératives," Acta Othopaedica Belgica, 1991, pp. 221-226, vol. 57, Suppl. I.

Senegas, "Mechanical Supplementation by Non-Rigid Fixation in Degenerative Intervertebral Lumbar Segments: the Wallis System," Eur. Spine J., 2002, p. S164-S169, vol. 11, Suppl. 2.

Senegas, "Rencontre," Maîtrise Orthopédique, May 1995, pp. 1-3, No. 44.

Serhan, "Spinal Implants: Past, Present, and Future," 19th International IEEE/EMBS Conference, Oct. 30-Nov. 2, 1997, pp. 2636-2639, Chicago, Illinois.

Spadea et al., "Interspinous Fusion for the Treatment of Herniated Intervertebral Discs: Utilizing a Lumbar Spinous Process as a Bone Graft," Annals of Surgery, 1952, pp. 982-986, vol. 136, No. 6.

Sulzer Innotec, "DIAM—Modified CAD Geometry and Meshing," date unknown.

Taylor et al., "Analyse d'une expérience clinique d'un implant postérieur amortissant," Rachis Revue de Pathologie Vertébrale, Oct./Nov. 1999, vol. 11, No. 4-5, Gieda Inter Rachis.

Taylor et al., "Surgical Requirement for the Posterior Control of the Rotational Centers," date unknown.

Taylor et al., "Technical and Anatomical Considerations for the Placement of a Posterior Interspinous Stabilizer," 2004, pp. 1-10, Medtronic Sofamor Danek USA, Inc., Memphis, Tennessee.

Taylor, "Biomechanical Requirements for the Posterior Control of the Centers of Rotation," Swiss Spine Institute International Symposium: Progress in Spinal Fixation, Jun. 21-22, 2002, pp. 1-2, Swiss Spine Institute, Bern, Switzerland.

Taylor, "Non-Fusion Technologies of the Posterior Column: A New Posterior Shock Absorber," International Symposium on Intervertebral Disc Replacement and Non-Fusion-Technology, May 3-5, 2001, Spine Arthroplasty.

Taylor, "Posterior Dynamic Stabilization using the DIAM (Device for Intervertebral Assisted Motion)," date unknown, pp. 1-5.

Taylor, "Présentation à un an d'un dispositif amortissant d'assistance discale," 5èmes journées Avances & Controverses en pathologie rachidienne, Oct. 1-2, 1998, Faculté Libre de Médecine de Lille.

Tsuji et al., "Ceramic Interspinous Block (CISB) Assisted Anterior Interbody Fusion," J. Spinal Disorders, 1990, pp. 77-86, vol. 3, No. 1.

Vangilder, "Interspinous, Laminar, and Facet Posterior Cervical Bone Fusions," Techniques in Spinal Fusion and Stabilization, Hitchon et al., eds., 1995, pp. 135-146, Ch. 13, Thieme, New York.

Voydeville et al., "Experimental Lumbar Instability and Artificial Ligament," Eur. J. Orthop. Surg. Traumatol., Jul. 15, 2000, pp. 167-176, vol. 10.

Voydeville et al., "Lumbar Instability Treated by Intervertebral Ligamentoplasty with Smooth Wedges," Orthopédie Traumatologie, 1992, pp. 259-264, vol. 2, No. 4.

Waldemar Link, "Spinal Surgery: Instrumentation and Implants for Spinal Surgery," 1981, Link America Inc., New Jersey.

Wiltse et al., "The Treatment of Spinal Stenosis," Clinical Orthopaedics and Related Research, Urist, ed., Mar.-Apr. 1976, pp. 83-91, No. 115.

Wisneski et al., "Decompressive Surgery for Lumbar Spinal Stenosis," Seminars in Spine Surgery, Wiesel, ed., Jun. 1994, pp. 116-123, vol. 6, No. 2.

Zdeblick et al., "Two-Point Fixation of the Lumbar Spine Differential Stability in Rotation," SPINE, 1991, pp. S298-S301, vol. 16, No. 6, Supplement.

Zucherman et al., "Clinical Efficacy of Spinal Instrumentation in Lumbar Degenerative Disc Disease," Spine, Jul. 1992, pp. 834-837, vol. 17, No. 7.

* cited by examiner

INTEROSTEOTIC IMPLANT

FIELD OF THE DISCLOSURE

The present disclosure relates generally to orthopedics and orthopedic surgery. More specifically, the present disclosure relates to devices used to support adjacent bones.

BACKGROUND

In human anatomy, the spine is a generally flexible column that can take tensile and compressive loads. The spine also allows bending motion and provides a place of attachment for keels, muscles and ligaments. Generally, the spine is divided into three sections: the cervical spine, the thoracic spine and the lumbar spine. The sections of the spine are made up of individual bones called vertebrae. Also, the vertebrae are separated by intervertebral discs, which are situated between adjacent vertebrae.

The intervertebral discs function as shock absorbers and as joints. Further, the intervertebral discs can absorb the compressive and tensile loads to which the spinal column may be subjected. At the same time, the intervertebral discs can allow adjacent vertebral bodies to move relative to each other a limited amount, particularly during bending, or flexure, of the spine. Thus, the intervertebral discs are under constant muscular and/or gravitational pressure and generally, the intervertebral discs are the first parts of the lumbar spine to show signs of deterioration.

Facet joint degeneration is also common because the facet joints are in almost constant motion with the spine. In fact, facet joint degeneration and disc degeneration frequently occur together. Generally, although one may be the primary problem while the other is a secondary problem resulting from the altered mechanics of the spine, by the time surgical options are considered, both facet joint degeneration and disc degeneration typically have occurred. For example, the altered mechanics of the facet joints and/or intervertebral disc may cause spinal stenosis, degenerative spondylolisthesis, and degenerative scoliosis.

DETAILED DESCRIPTION OF THE DRAWINGS

An implant is disclosed and can include a body and a plurality of pellets disposed within the body. The implant can be moved between an unmolded, relaxed configuration wherein the body is not conformed to a bone and a molded, relaxed configuration wherein the body is at least partially conformed to the bone.

In another embodiment, an implant is disclosed and can include a conformable body that can contain a plurality of pellets and a fluid. The implant can be configured from a malleable configuration to a substantially rigid configuration by removing fluid from the body.

In yet another embodiment, a method of treating a spine is disclosed and includes molding an implant to at least partially conform to at least one bone. The implant can include a body and a plurality of pellets within the body. The method also includes tightening the body around the pellets to create a substantially rigid structure that can be in engagement within the bone.

In still another embodiment, a kit is disclosed and can include an implant, an implant pushing device, and an implant pulling device. The implant can include a body and a plurality of pellets within the body. Further, the implant pushing device and the implant pulling device can be configured to stretch the body of the implant around the pellets and close-pack the pellets.

Description of Relevant Anatomy

Figure 1:
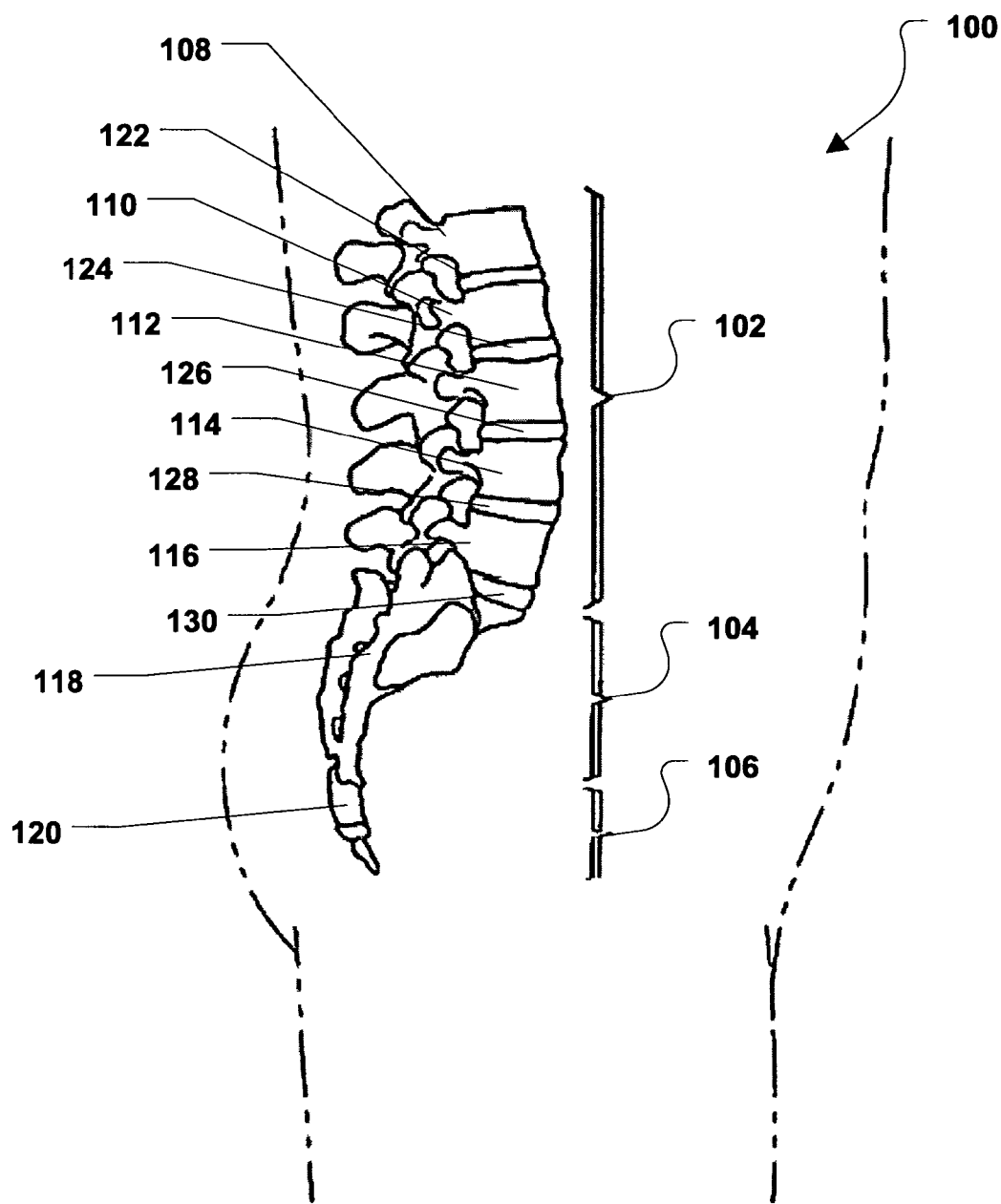
FIG. 1 is a lateral view of a portion of a vertebral column.

Referring initially to FIG. 1, a portion of a vertebral column, designated 100, is shown. As depicted, the vertebral column 100 includes a lumbar region 102, a sacral region 104, and a coccygeal region 106. As is known in the art, the vertebral column 100 also includes a cervical region and a thoracic region. For clarity and ease of discussion, the cervical region and the thoracic region are not illustrated.

As shown in FIG. 1, the lumbar region 102 includes a first lumbar vertebra 108, a second lumbar vertebra 110, a third lumbar vertebra 112, a fourth lumbar vertebra 114, and a fifth lumbar vertebra 116. The sacral region 104 includes a sacrum 118. Further, the coccygeal region 106 includes a coccyx 120.

As depicted in FIG. 1, a first intervertebral lumbar disc 122 is disposed between the first lumbar vertebra 108 and the second lumbar vertebra 110. A second intervertebral lumbar disc 124 is disposed between the second lumbar vertebra 110 and the third lumbar vertebra 112. A third intervertebral lumbar disc 126 is disposed between the third lumbar vertebra 112 and the fourth lumbar vertebra 114. Further, a fourth intervertebral lumbar disc 128 is disposed between the fourth lumbar vertebra 114 and the fifth lumbar vertebra 116. Additionally, a fifth intervertebral lumbar disc 130 is disposed between the fifth lumbar vertebra 116 and the sacrum 118.

In a particular embodiment, if one of the intervertebral lumbar discs 122, 124, 126, 128, 130 is diseased, degenerated, damaged, or otherwise in need of repair, augmentation or treatment, that intervertebral lumbar disc 122, 124, 126, 128, 130 can be treated in accordance with one or more of the embodiments described herein.

Figure 2:
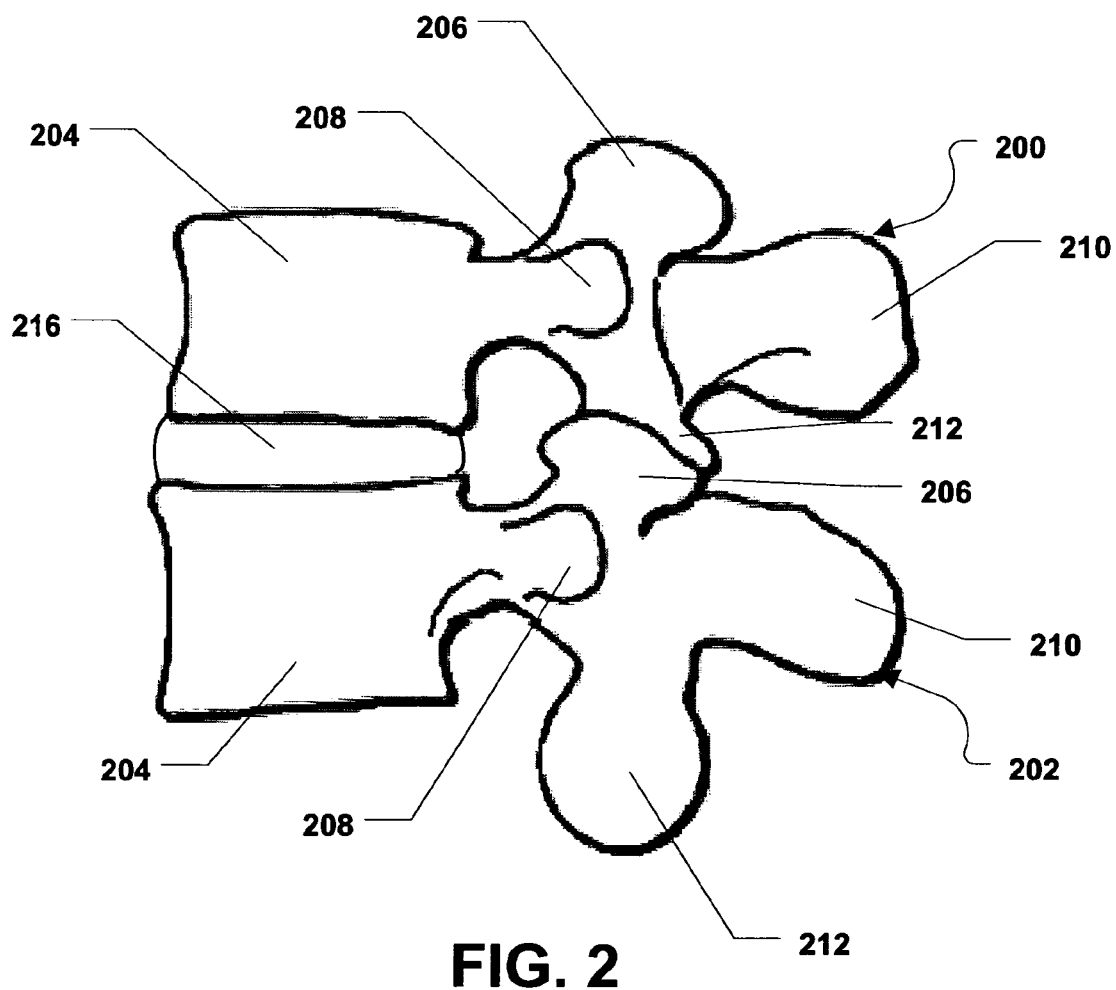
FIG. 2 is a lateral view of a pair of adjacent vertebrae.

FIG. 2 depicts a detailed lateral view of two adjacent vertebrae, e.g., two of the lumbar vertebra 108, 110, 112, 114, 116 shown in FIG. 1. FIG. 2 illustrates a superior vertebra 200 and an inferior vertebra 202. As shown, each vertebra 200, 202 includes a vertebral body 204, a superior articular process 206, a transverse process 208, a spinous process 210 and an inferior articular process 212. FIG. 2 further depicts an intervertebral disc 216 between the superior vertebra 200 and the inferior vertebra 202.

Figure 3:
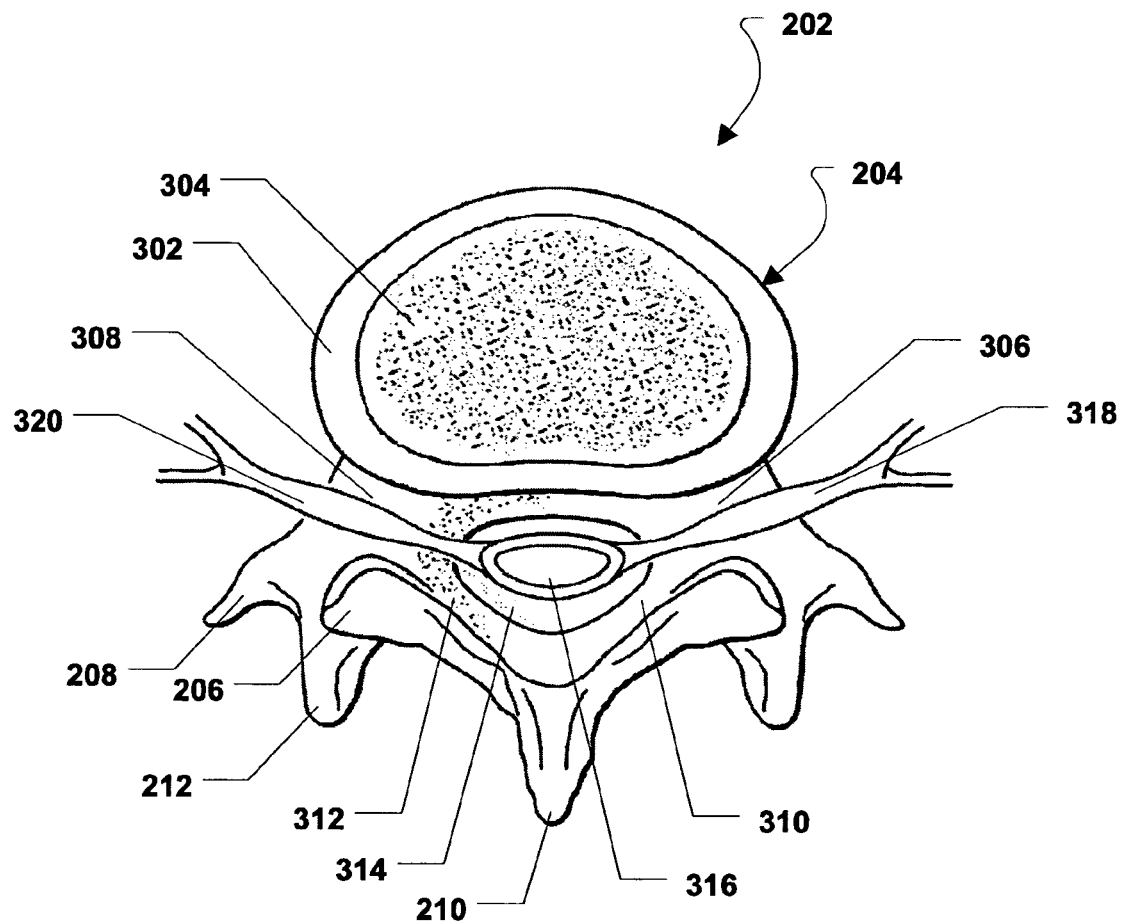
FIG. 3 is a top plan view of a vertebra.

Referring to FIG. 3, a vertebra, e.g., the inferior vertebra 202 (FIG. 2), is illustrated. As shown, the vertebral body 204 of the inferior vertebra 202 includes a cortical rim 302 composed of cortical bone. Also, the vertebral body 204 includes cancellous bone 304 within the cortical rim 302. The cortical rim 302 is often referred to as the apophyseal rim or apophyseal ring. Further, the cancellous bone 304 is softer than the cortical bone of the cortical rim 302.

As illustrated in FIG. 3, the inferior vertebra 202 further includes a first pedicle 306, a second pedicle 308, a first lamina 310, and a second lamina 312. Further, a vertebral foramen 314 is established within the inferior vertebra 202. A spinal cord 316 passes through the vertebral foramen 314. Moreover, a first nerve root 318 and a second nerve root 320 extend from the spinal cord 316.

It is well known in the art that the vertebrae that make up the vertebral column have slightly different appearances as they range from the cervical region to the lumbar region of the vertebral column. However, all of the vertebrae, except the first and second cervical vertebrae, have the same basic structures, e.g., those structures described above in conjunction with FIG. 2 and FIG. 3. The first and second cervical vertebrae are structurally different than the rest of the vertebrae in order to support a skull.

Description of a First Embodiment of an Implant

Referring to FIG. 4 through FIG. 7, a first implant is shown and is generally designated 400. As shown, the implant 400 can include a hollow, body 402. In a particular embodiment, the body 402 can be made from one or more biocompatible materials. For example, the materials can be silicone, polyurethane, polycarbonate urethane, polyethylene terephthalate, silicone copolymers, polyolefin, or any combination thereof.

Figure 4:
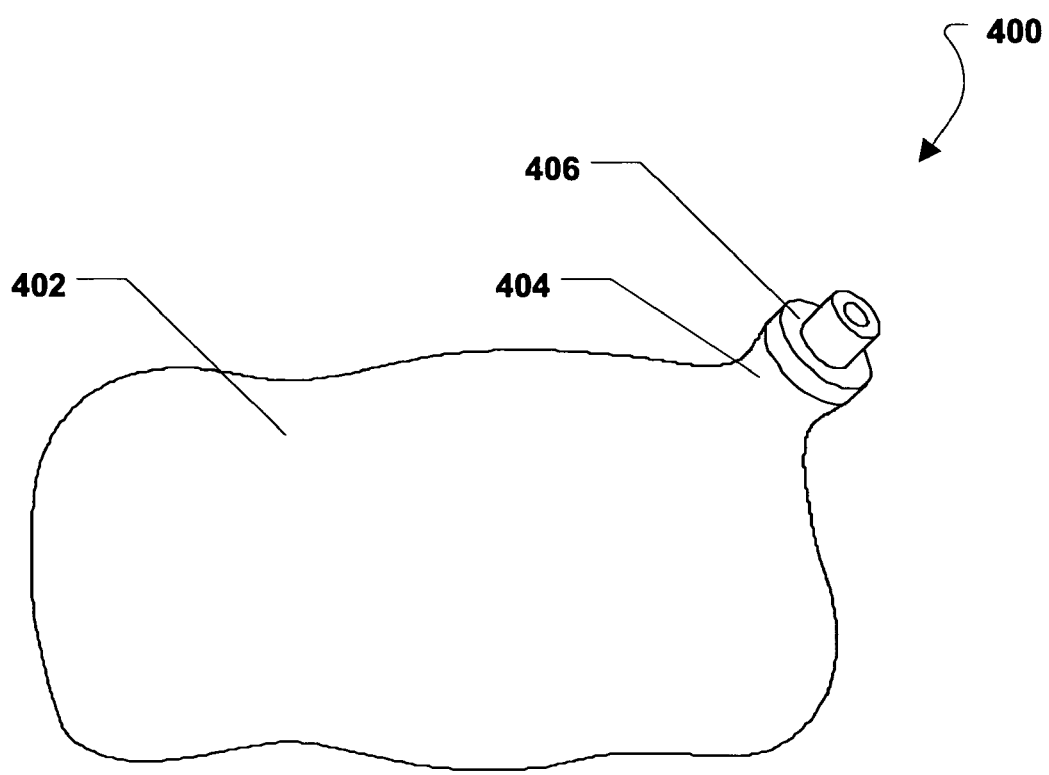
FIG. 4 is a view of a first implant in an unmolded, relaxed configuration.
Figure 5:
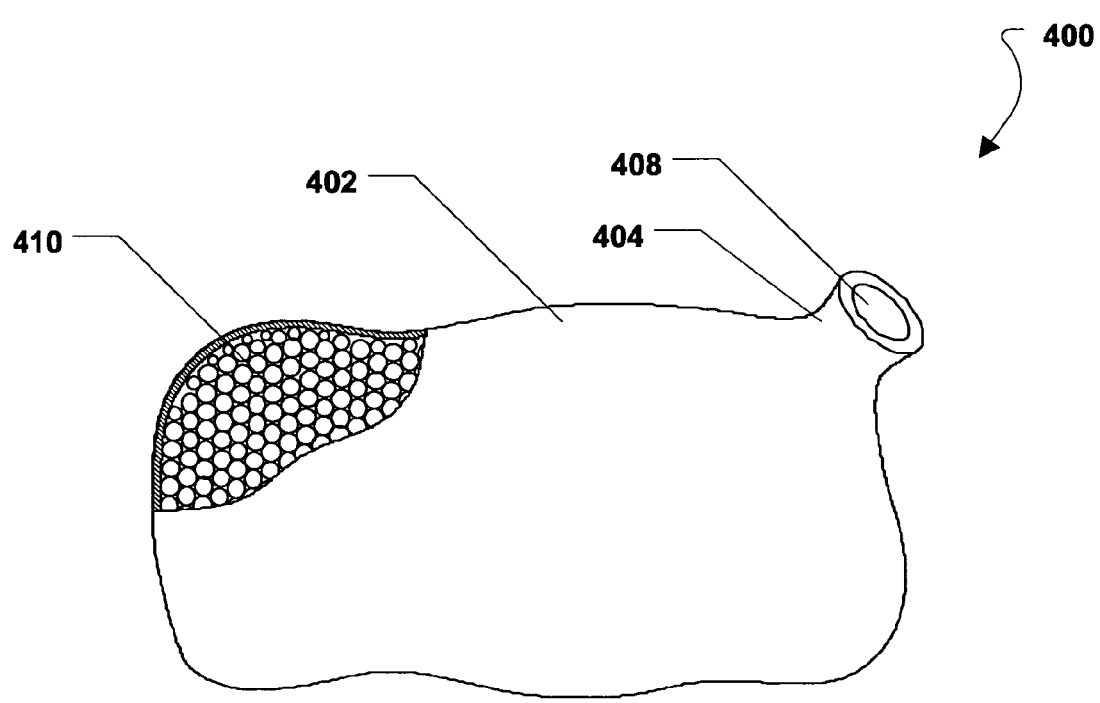
FIG. 5 is a partial cut-away view of the first implant.

As illustrated in FIG. 4, the body 402 of the implant 400 can further include a stem 404 and a valve 406 can be disposed within the stem 404. FIG. 5 indicates that the stem 404 can be formed with an opening 408. In a particular embodiment, the valve 406 can be installed in the opening 408 of the stem 404. FIG. 5 also shows that the body 402 can be filled with a plurality of pellets 410.

In a particular embodiment, the pellets 410 can be a filler material. The pellets 410 can also include granules, powder, particles, chunks, pieces, or a combination thereof.

In a particular embodiment, the pellets 410 can be generally spherical, generally elliptical, generally pyramidal, generally conical, generally frustal, generally cubic, generally polyhedral, or a combination thereof. In a particular embodiment, the pellets 410 can be made from one or more biocompatible materials. For example, the materials can be metal containing materials, polymer materials, or composite materials that include metals, polymers, or combinations of metals and polymers.

The pellets 410 can range in size from micro-size particles to chunks that measure one or more millimeters. In a specific embodiment, the pellets 410 can have an overall dimension, e.g., a length, width, height, or a combination thereof, that can be in a range of fifty micrometers (50 μm) to five millimeters (5 mm). More specifically, the pellets 410 can include an overall dimension that can be in a range of 250 micrometers (250 μm) to two and one-half millimeters (2.5 mm).

Regardless of shape or size, the pellets 410 can have an aspect ratio, i.e., a ratio of one dimension to another dimension, that can be in a range of one (1) to fifty (50). More specifically, the pellets 410 can have an aspect ratio that can be in a range of one (1) to five (5). The aspect ratio can be a ratio of length to width, a ratio of length to height, a ratio of width to length, a ratio of width to height, a ratio of height to length, a ratio of height to width, or a combination thereof.

In a particular embodiment, the metal containing materials can be metals. Further, the metal containing materials can be ceramics. Also, the metals can be pure metals or metal alloys. The pure metals can include titanium. Moreover, the metal alloys can include stainless steel, a cobalt-chrome-molybdenum alloy, e.g., ASTM F-999 or ASTM F-75, a titanium alloy, or a combination thereof.

The polymer materials can include polyurethane, polyolefin, polyaryletherketone (PAEK), silicone, hydrogel, or a combination thereof. Further, the polyolefin materials can include polypropylene, polyethylene, halogenated polyolefin, flouropolyolefin, or a combination thereof.

The polyaryletherketon (PAEK) materials can include polyetherketone (PEK), polyetheretherketone (PEEK), polyetherketoneketone (PEKK), polyetherketoneetherketoneketone (PEKEKK), or a combination thereof.

The hydrogels can include polyacrylamide, poly-N-isopropylacrylamine, polyvinyl methylether, polyvinyl alcohol, polyethyl hydroxyethyl cellulose, poly (2-ethyl) oxazoline, polyethyleneoxide, polyethylglycol, polyethylene glycol, polyacrylic acid, polyacrylonitrile, polyvinylacrylate, polyvinylpyrrolidone, or a combination thereof.

In a particular embodiment, the ceramics can include calcium phosphate, hydroxyapatite, calcium sulfate, bioactive glass, or a combination thereof.

The body can also contain a fluid such as, for example, air or saline, in order to maintain the pellets in a loose-packed, malleable configuration.

Figure 6:
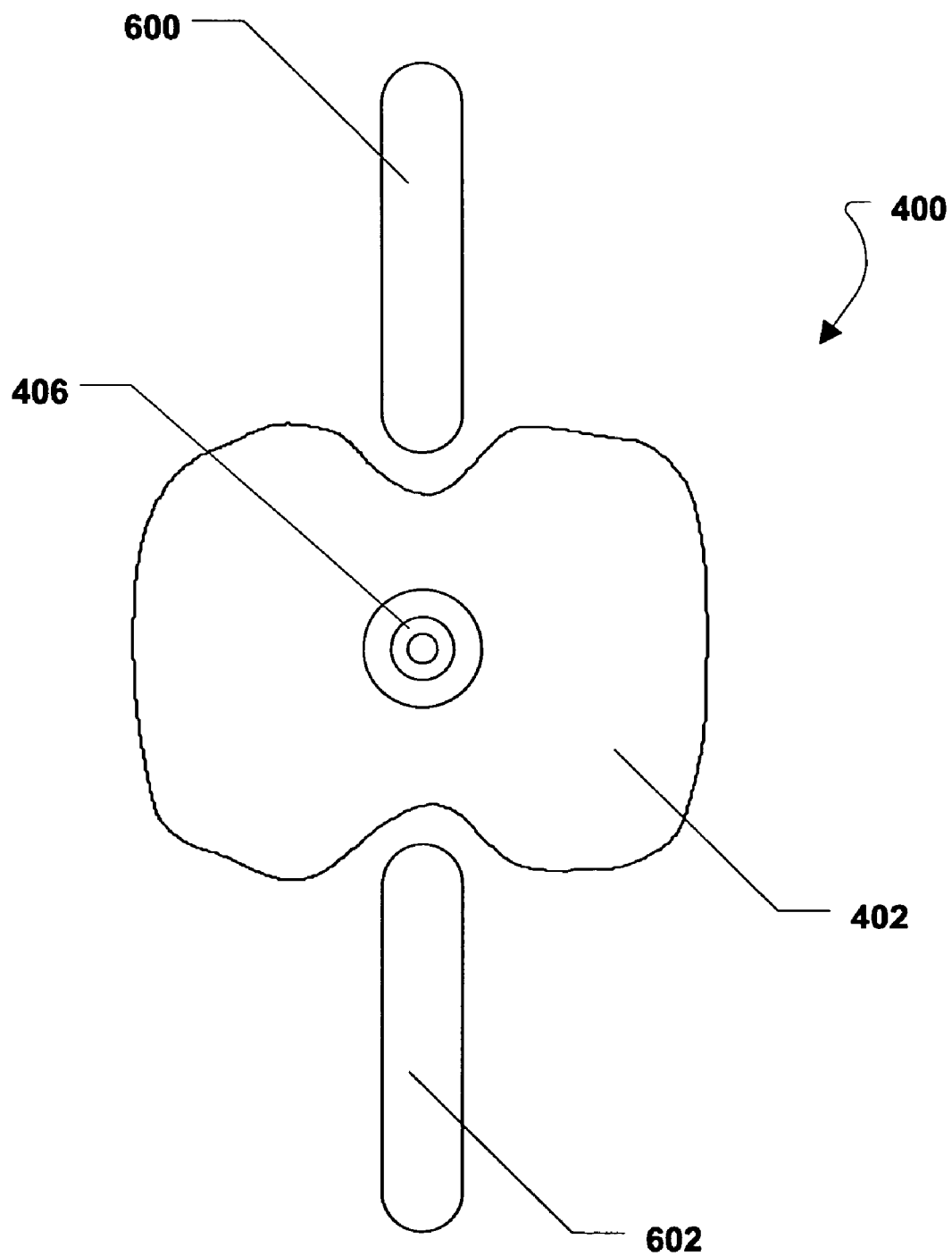
FIG. 6 is a view of the first implant in a molded, relaxed configuration between adjacent spinous processes.
Figure 7:
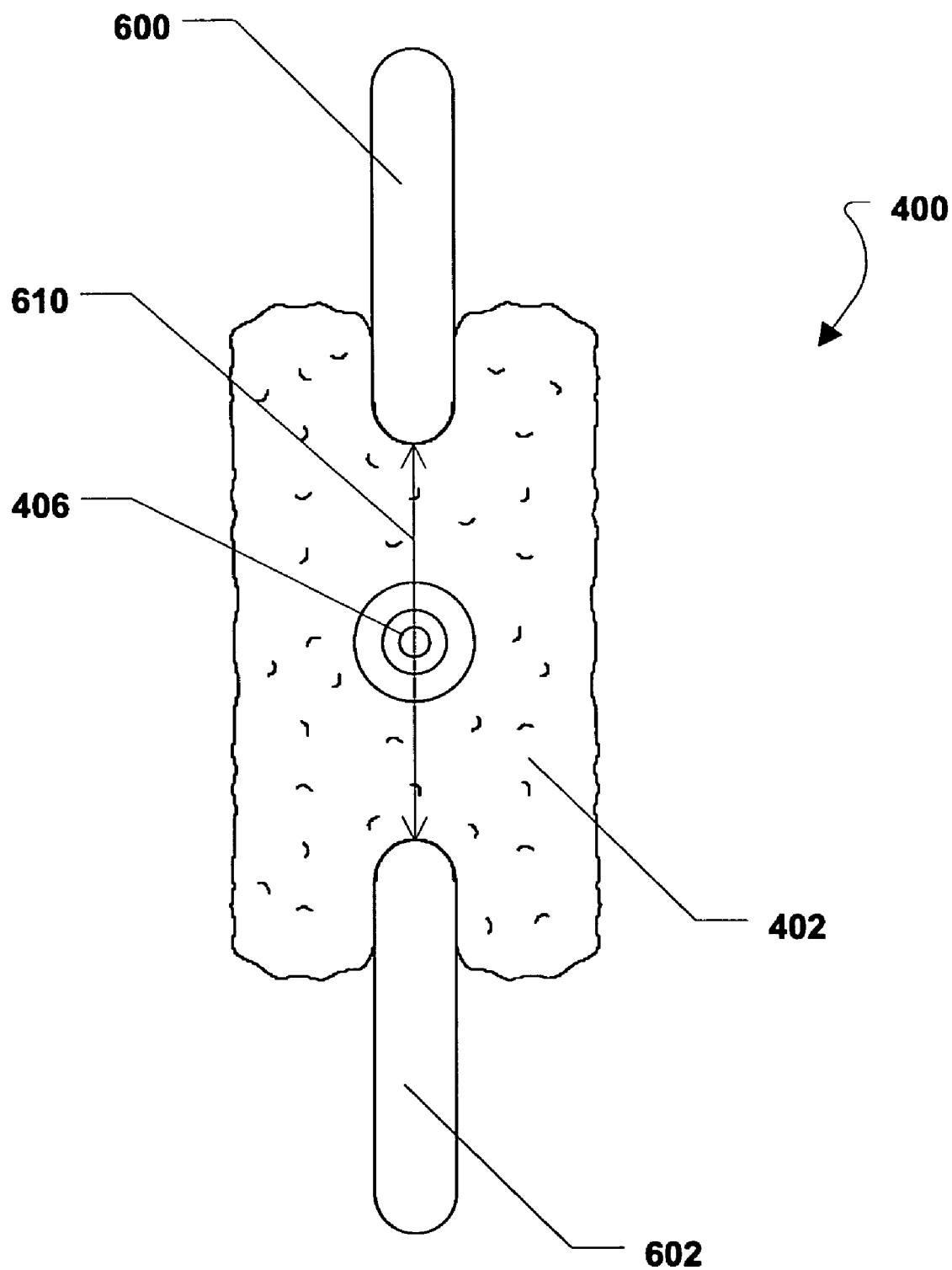
FIG. 7 is a view of the first implant in a molded, compressed configuration between adjacent spinous processes.
Figure 8:
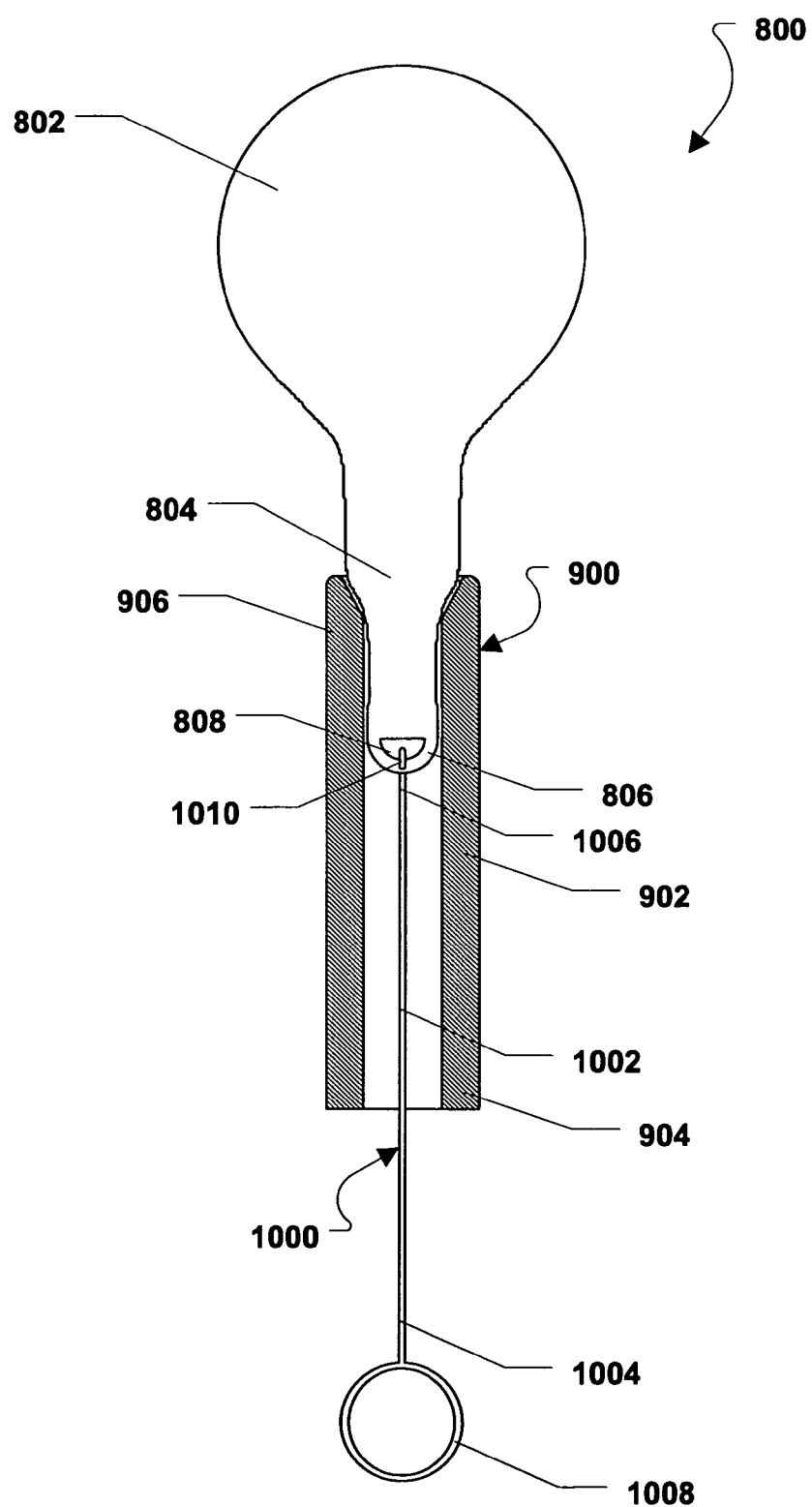
FIG. 8 is a view of a second implant in an unmolded, relaxed configuration.

As shown in FIG. 6 and FIG. 7, the implant 400 can be installed between adjacent bones or groups of bones such as, for example, a superior spinous process 600 and an inferior spinous process 602. Further, the implant 400 can be moved from an unmolded, relaxed configuration, shown in FIG. 4 and FIG. 5, to a molded, relaxed configuration, shown in FIG. 6. In a particular embodiment, the implant 400 can be manually moved to the molded, relaxed configuration. For example, the implant can be moved to a shape that closely resembles a final shape desired by the user, e.g., a surgeon.

After the implant 400 is moved to the molded, relaxed configuration, a vacuum line (not shown) can be coupled to the valve 406. Thereafter, air within the body 402 of the implant 402 can be evacuated and the body 402 can be moved to a molded, compressed configuration, shown in FIG. 7, in which the pellets 410 within the body 402 can be close-packed. In the molded, compressed configuration, the pellets 410 within the body 402 form a relatively rigid construct that can support the adjacent spinous processes 602, 604 and substantially prevent a distance 610 there between from decreasing - other than slight temporary decreases due to the elasticity of the pellets 410 within the implant 400. After the implant 400 is moved to the molded, compressed configuration, the vacuum line (not shown) can be removed.

In the unmolded, relaxed configuration the pellets 410 are loose-packed and the body 402 does not conform to a bone, e.g., a spinous process. In the molded, relaxed configuration, the pellets 410 remain loose-packed, but the body 402 at least partially conforms to a bone. Further, in the molded, compressed configuration, the pellets 410 are close-packed and the body 402 at least partially conforms to a bone. In an exemplary embodiment, the body can contain a curable material which, when cured, can substantially maintain the pellets in the molded configuration. The curable material can be chosen from art-recognized materials that can be cured in vivo, such as a material that can be cured in situ, such as a moisture curable material. In a certain embodiment, the curable material can comprise a silicone material In a particular embodiment, in the unmolded, relaxed configuration a ratio of a volume of pellets 410 to an interior volume of the body 402 can be less than or equal to 0.9. Further, in the unmolded, relaxed configuration a ratio of a volume of pellets 410 to an interior volume of the body 402 can be less than or equal to 0.75. In the molded, compressed configuration a ratio of a volume of pellets 410 to an interior volume of the body 402 can be greater than or equal to 0.9. Moreover, in the molded, compressed configuration a ratio of a volume of pellets 410 to an interior volume of the body 402 can be greater than or equal to 0.95.

In another embodiment, a distractor can be used to increase the distance 610 between the superior spinous process 600 and the inferior spinous process 602 and the implant 400 can be placed within the distracted superior spinous process 600 and the inferior spinous process 602. After the implant 400 is moved to the molded, compressed configuration, as described herein, the distractor can be removed and the implant 400 can support the superior spinous process 600 and the inferior spinous process 602 and substantially prevent the distance 610 between the superior spinous process 600 and the inferior spinous process 602 from returning to a pre-distraction value. Description of a Second Embodiment of an Implant Referring to FIG. 8 through FIG. 12, a second implant is shown and is generally designated 800. As shown, the implant 800 can include a hollow, body 802. In a particular embodiment, the body 802 can be made from one or more biocompatible materials. For example, the materials can be silicone, polyurethane, polycarbonate urethane, polyethylene terephthalate, silicone copolymers, polyolefin, or any combination thereof.

Figure 9:
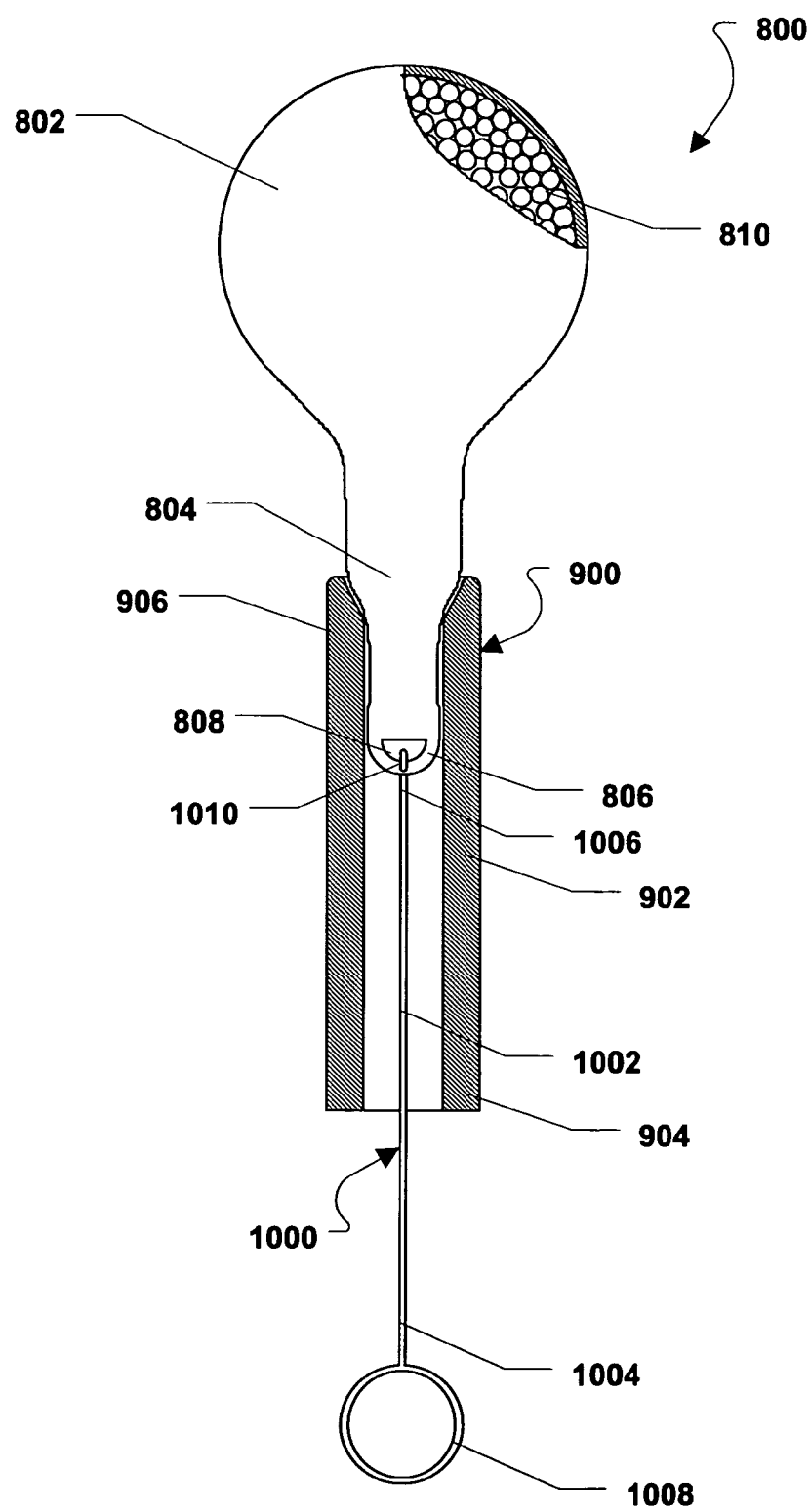
FIG. 9 is a partial cut-away view of the second implant.

As illustrated, the implant 800 can further include a stem 804 that extends from the body 802. Further, the stem 804 can include an end 806. The end 806 of the stem 804 can include an eyelet 808 configured to receive a hook attached to a pulling device. FIG. 9 shows that the body 802 can be filled with filled with a plurality of pellets 810.

In a particular embodiment, the pellets 810 can be a filler material. The pellets 810 can also include granules, powder, particles, chunks, pieces, or a combination thereof.

In a particular embodiment, the pellets 810 can be generally spherical, generally elliptical, generally pyramidal, generally conical, generally frustal, generally cubic, generally polyhedral, or a combination thereof. In a particular embodiment, the pellets 810 can be made from one or more biocompatible materials. For example, the materials can be metal containing materials, polymer materials, or composite materials that include metals, polymers, or combinations of metals and polymers.

The pellets 810 can range in size from micro-size particles to chunks that measure one or more millimeters. In a specific embodiment, the pellets 810 can have an overall dimension, e.g., a length, width, height, or a combination thereof, that can be in a range of fifty micrometers (50 μm) to five millimeters (5 mm). More specifically, the pellets 810 can include an overall dimension that can be in a range of 250 micrometers (250 μm) to two and one-half millimeters (2.5 mm).

Regardless of shape or size, the pellets 810 can have an aspect ratio, i.e., a ratio of one dimension to another dimension, that can be in a range of one (1) to fifty (50). More specifically, the pellets 810 can have an aspect ratio that can be in a range of one (1) to five (5). The aspect ratio can be a ratio of length to width, a ratio of length to height, a ratio of width to length, a ratio of width to height, a ratio of height to length, a ratio of height to width, or a combination thereof.

In a particular embodiment, the metal containing materials can be metals. Further, the metal containing materials can be ceramics. Also, the metals can be pure metals or metal alloys. The pure metals can include titanium. Moreover, the metal alloys can include stainless steel, a cobalt-chrome-molybdenum alloy, e.g., ASTM F-999 or ASTM F-75, a titanium alloy, or a combination thereof.

The polymer materials can include polyurethane, polyolefin, polyaryletherketone (PAEK), silicone, hydrogel, or a combination thereof. Further, the polyolefin materials can include polypropylene, polyethylene, halogenated polyolefin, flouropolyolefin, or a combination thereof.

The polyaryletherketon (PAEK) materials can include polyetherketone (PEK), polyetheretherketone (PEEK), polyetherketoneketone (PEKK), polyetherketoneetherketoneketone (PEKEKK), or a combination thereof.

The hydrogels can include polyacrylamide, poly-N-isopropylacrylamine, polyvinyl methylether, polyvinyl alcohol, polyethyl hydroxyethyl cellulose, poly (2-ethyl) oxazoline, polyethyleneoxide, polyethylglycol, polyethylene glycol, polyacrylic acid, polyacrylonitrile, polyvinylacrylate, polyvinylpyrrolidone, or a combination thereof.

In a particular embodiment, the ceramics can include calcium phosphate, hydroxyapatite, calcium sulfate, bioactive glass, or a combination thereof.

The body can also contain a fluid such as, for example, air or saline, in order to maintain the pellets in a loose-packed, malleable configuration.

FIG. 8 through FIG. 11 further depict an implant pushing device 900. The implant pushing device 900 can include a body 902. The body 902 can include a proximal end 904 and a distal end 906. Further, the body 902 can be formed with an interior chamber 908. In a particular embodiment, the implant pushing device 900 can be fitted around the stem 804 that extends from the body 802 of the implant 800.

FIG. 8 through FIG. 11 also show an implant pulling device 1000. The implant pulling device 1000 includes a body 1002. The body 1002 can include a proximal end 1004 and a distal end 1006. Further, a ring 1008 can be attached to the proximal end 1004 of the implant pulling device 1000. During operation, a user can place a finger through the ring 1008. As illustrated, the distal end 1006 can form a hook 1010. The hook 1010 can engage the eyelet 808 formed in the end 806 of the stem 804 that extends from the body 802 of the implant 800.

Figure 10:
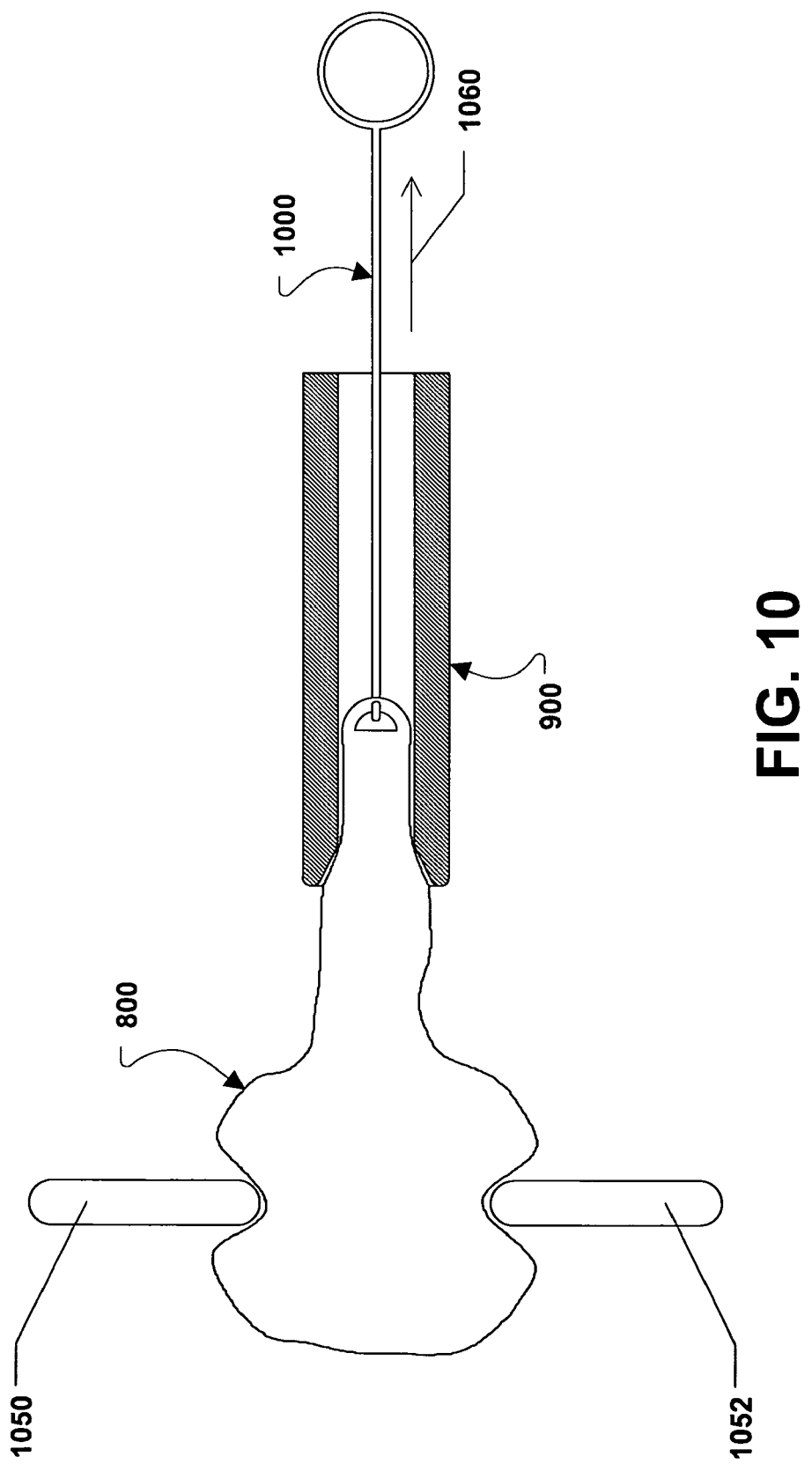
FIG. 10 is a view of the second implant in a molded, relaxed configuration between adjacent spinous processes.
Figure 11:
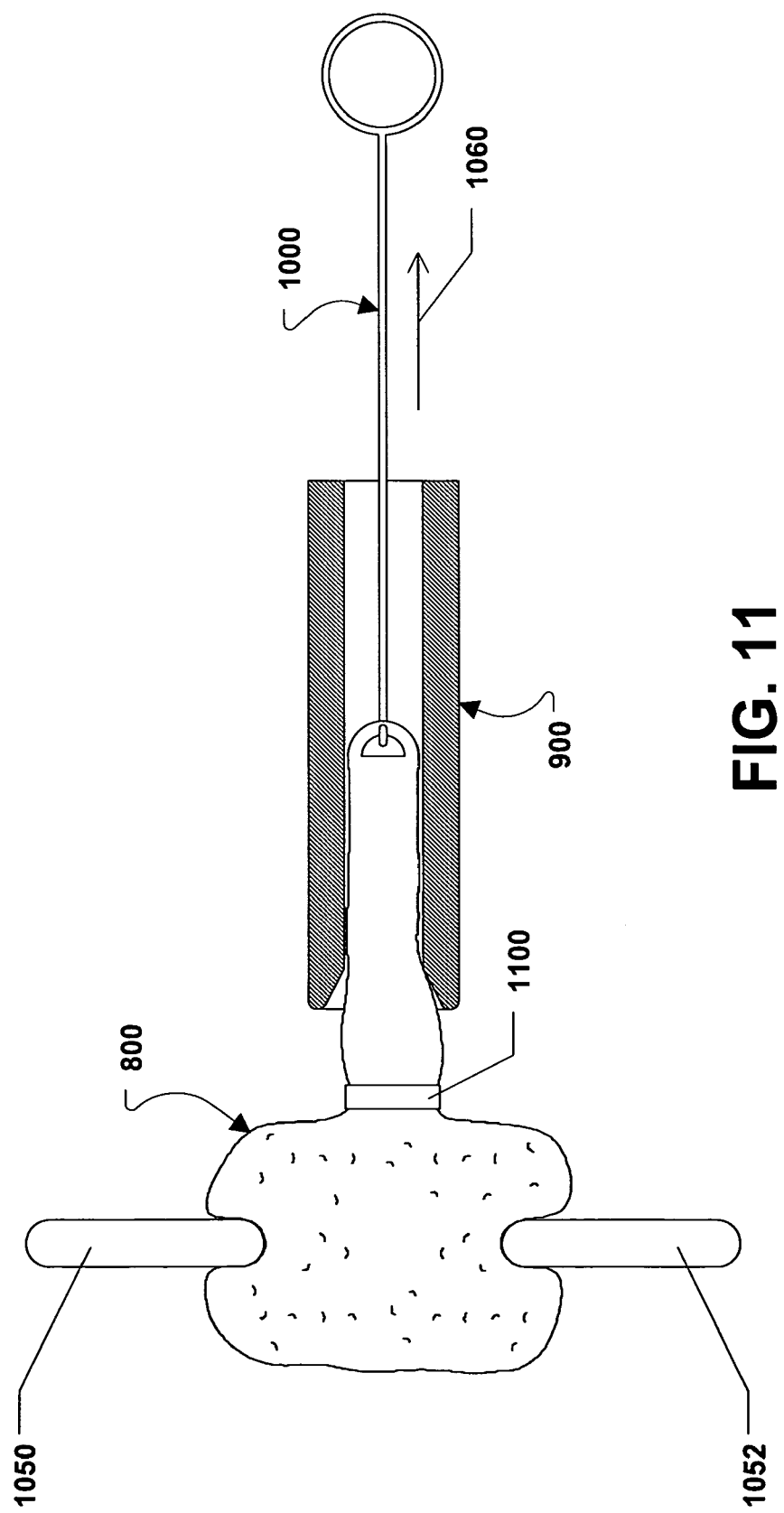
FIG. 11 is a view of the second implant in a molded, compressed configuration between adjacent spinous processes.
Figure 12:
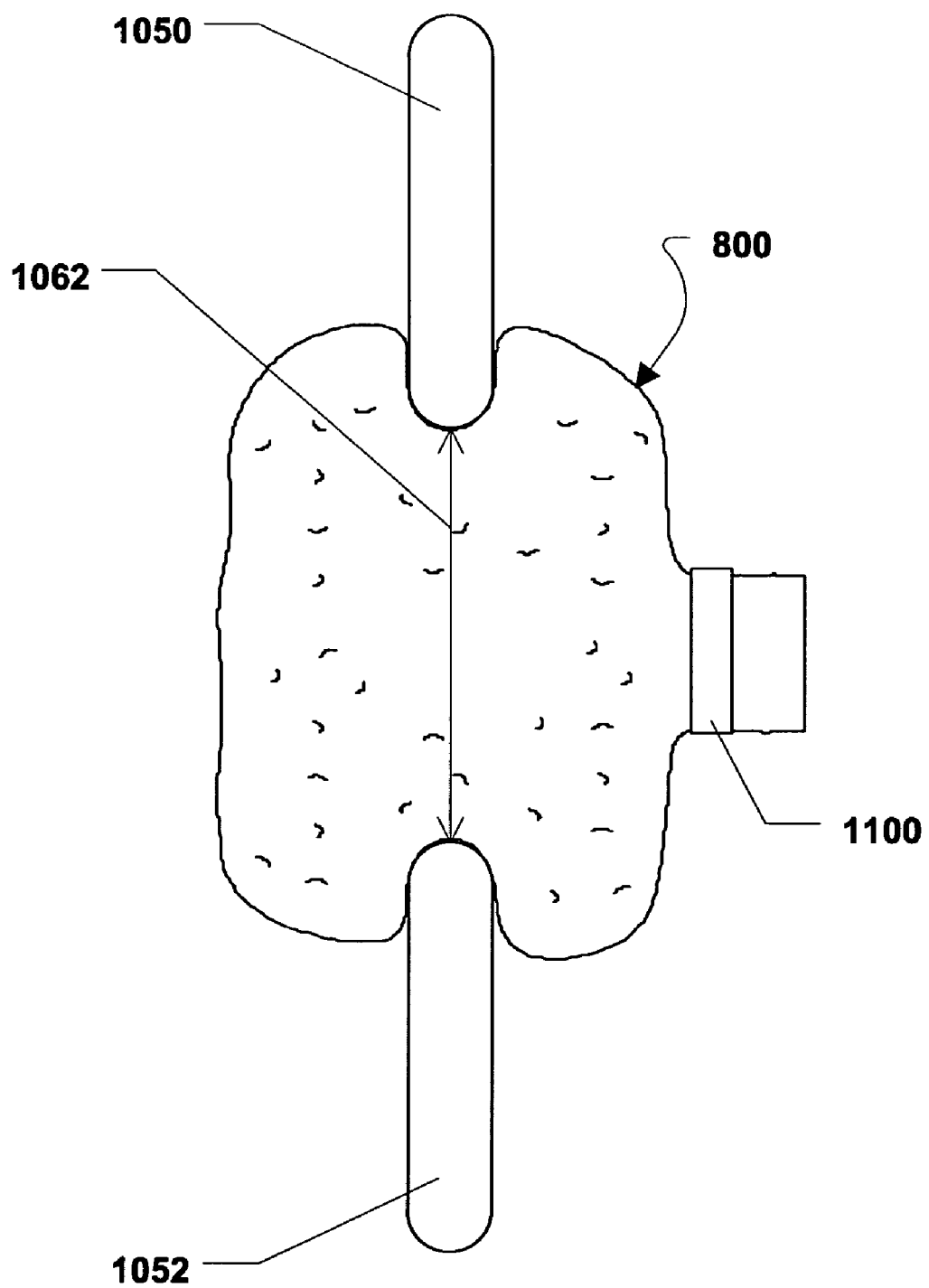
FIG. 12 is another view of the second implant in a molded, compressed configuration between adjacent spinous processes.
Figure 13:
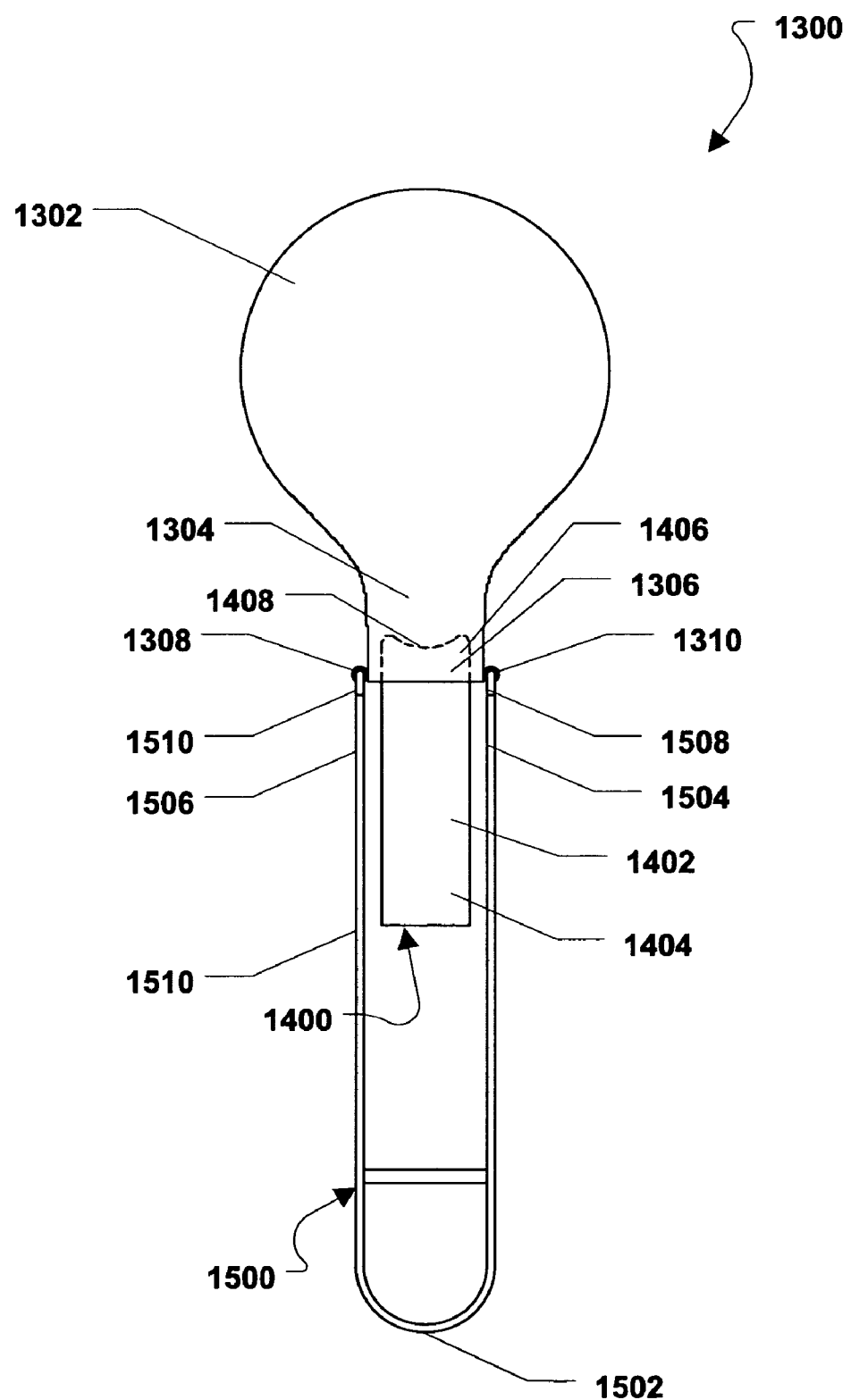
FIG. 13 is a view of a third implant in an unmolded, relaxed configuration.

As shown in FIG. 10 through FIG. 12, the implant 800 can be installed between adjacent bones or groups of bones such as, for example, a superior spinous process 1050 and an inferior spinous process 1052. Further, the implant 800 can be moved from an unmolded, relaxed configuration, shown in FIG. 8 and FIG. 9, to a molded, relaxed configuration, shown in FIG. 10. In a particular embodiment, the implant 800 can be manually moved to the molded, relaxed configuration. For example, the implant can be moved to a shape that closely resembles a final shape desired by the user, e.g., a surgeon.

After the implant 800 is moved to the molded, relaxed configuration, the implant pushing device 900 can be inserted around the stem 804 of the implant 800. Further, the implant pulling device 1000 can be hooked to the stem 804 of the implant 800. Thereafter, the implant pulling device 1000 can be moved relative to the implant pushing device 900, as indicated by arrow 1060, in order to stretch the body 802 of the implant 800 around the pellets 810. The body 802 of the implant can include a port (not shown) or a valve (not shown) that can be configured to allow air to pass through the body 802 as the body 802 is stretched around the pellets 810. Alternatively, the body 802 can be porous and the porosity of the body 802 can allow air to pass through the body 802 as the body 802 is stretched around the pellets 810.

After the body 802 is stretched, as indicated, a band 1100 can be placed around the stem 804 of the body 802 in order to seal the body 802 and prevent the pellets 810 from being expelled from within the body 802. The elasticity of the body 802 can compress the pellets 810 and cause the pellets 810 within the body 802 to be close-packed.

Accordingly, the implant 800 can be moved from the molded, relaxed configuration to a molded, compressed configuration. In the molded, compressed configuration, the pellets 810 within the body 802 can form a relatively rigid construct that can support the adjacent spinous processes 1050, 1052 and substantially prevent a distance 1062 there between from decreasing - other than slight temporary decreases due to the elasticity of the pellets 810 within the implant 800. After the implant 800 is moved to the molded, compressed configuration, the vacuum line (not shown) can be removed.

In the unmolded, relaxed configuration the pellets 810 are loose-packed and the body 802 does not conform to a bone, e.g., a spinous process. In the molded, relaxed configuration, the pellets 810 remain loose-packed, but the body 802 at least partially conforms to a bone. Further, in the molded, compressed configuration, the pellets 810 are close-packed and the body 802 at least partially conforms to a bone. In an exemplary embodiment, the body can contain a curable material which, when cured, can substantially maintain the pellets in the molded configuration. The curable material can be chosen from art-recognized materials that can be cured in vivo, such as a material that can be cured in situ, such as a moisture curable material. In a certain embodiment, the curable material can comprise a silicone material In a particular embodiment, in the unmolded, relaxed configuration a ratio of a volume of pellets 810 to an interior volume of the body 802 can be less than or equal to 0.9. Further, in the unmolded, relaxed configuration a ratio of a volume of pellets 810 to an interior volume of the body 802 can be less than or equal to 0.75. In the molded, compressed configuration a ratio of a volume of pellets 810 to an interior volume of the body 802 can be greater than or equal to 0.9. Moreover, in the molded, compressed configuration a ratio of a volume of pellets 810 to an interior volume of the body 802 can be greater than or equal to 0.95

In another embodiment, a distractor can be used to increase the distance 1062 between the superior spinous process 1050 and the inferior spinous process 1052 and the implant 800 can be placed within the distracted superior spinous process 1050 and the inferior spinous process 1052. After the implant 800 is moved to the molded, compressed configuration, as described herein, the distractor can be removed and the implant 800 can support the superior spinous process 1050 and the inferior spinous process 1052 and substantially prevent the distance 1062 between the superior spinous process 1050 and the inferior spinous process 1052 from returning to a pre-distraction value.

Description of a Third Embodiment of an Implant

Referring to FIG. 13 through FIG. 17, a third implant is shown and is generally designated 1300. As shown, the implant 1300 can include a hollow, body 1302. In a particular embodiment, the body 1302 can be made from one or more biocompatible materials. For example, the materials can be silicone, polyurethane, polycarbonate urethane, polyethylene terephthalate, silicone copolymers, polyolefin, or any combination thereof.

Figure 14:
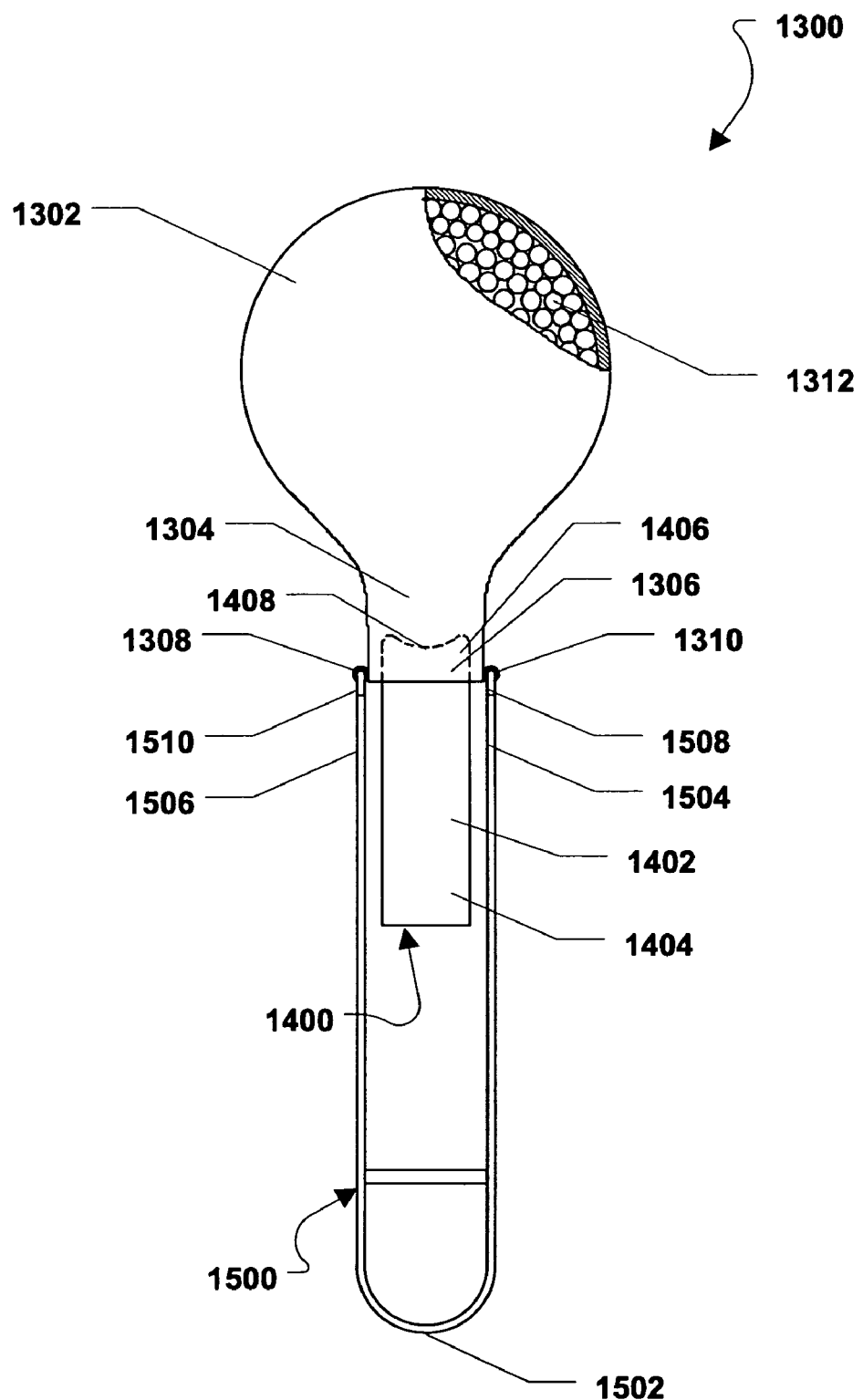
FIG. 14 is a partial cut-away view of the third implant.

As illustrated, the implant 1300 can further include a stem 1304 that extends from the body 1302. Further, the stem 1304 can include an end 1306. The end 1306 of the stem 1304 can include a first eyelet 1308 and a second eyelet 1310 that are configured to receive hooks attached to a pulling device. FIG. 14 shows that the body 1302 can be filled with filled with a plurality of pellets 1312.

In a particular embodiment, the pellets 1312 can be a filler material. The pellets 1312 can also include granules, powder, particles, chunks, pieces, or a combination thereof.

In a particular embodiment, the pellets 1312 can be generally spherical, generally elliptical, generally pyramidal, generally conical, generally frustal, generally cubic, generally polyhedral, or a combination thereof. In a particular embodiment, the pellets 1312 can be made from one or more biocompatible materials. For example, the materials can be metal containing materials, polymer materials, or composite materials that include metals, polymers, or combinations of metals and polymers.

The pellets 1312 can range in size from micro-size particles to chunks that measure one or more millimeters. In a specific embodiment, the pellets 1312 can have an overall dimension, e.g., a length, width, height, or a combination thereof, that can be in a range of fifty micrometers (50 μm) to five millimeters (5 mm). More specifically, the pellets 1312 can include an overall dimension that can be in a range of 250 micrometers (250 μm) to two and one-half millimeters (2.5 mm).

Regardless of shape or size, the pellets 1312 can have an aspect ratio, i.e., a ratio of one dimension to another dimension, that can be in a range of one (1) to fifty (50). More specifically, the pellets 1312 can have an aspect ratio that can be in a range of one (1) to five (5). The aspect ratio can be a ratio of length to width, a ratio of length to height, a ratio of width to length, a ratio of width to height, a ratio of height to length, a ratio of height to width, or a combination thereof.

In a particular embodiment, the metal containing materials can be metals. Further, the metal containing materials can be ceramics. Also, the metals can be pure metals or metal alloys. The pure metals can include titanium. Moreover, the metal alloys can include stainless steel, a cobalt-chrome-molybdenum alloy, e.g., ASTM F-999 or ASTM F-75, a titanium alloy, or a combination thereof.

The polymer materials can include polyurethane, polyolefin, polyaryletherketone (PAEK), silicone, hydrogel, or a combination thereof. Further, the polyolefin materials can include polypropylene, polyethylene, halogenated polyolefin, flouropolyolefin, or a combination thereof.

The polyaryletherketon (PAEK) materials can include polyetherketone (PEK), polyetheretherketone (PEEK), polyetherketoneketone (PEKK), polyetherketoneetherketoneketone (PEKEKK), or a combination thereof The hydrogels can include polyacrylamide, poly-N-isopropylacrylamine, polyvinyl methylether, polyvinyl alcohol, polyethyl hydroxyethyl cellulose, poly (2-ethyl) oxazoline, polyethyleneoxide, polyethylglycol, polyethylene glycol, polyacrylic acid, polyacrylonitrile, polyvinylacrylate, polyvinylpyrrolidone, or a combination thereof.

In a particular embodiment, the ceramics can include calcium phosphate, hydroxyapatite, calcium sulfate, bioactive glass, or a combination thereof.

The body can also contain a fluid such as, for example, air or saline, in order to maintain the pellets in a loose-packed, malleable configuration.

FIG. 13 through FIG. 16 further depict an implant pushing device 1400. The implant pushing device 1400 can include a body 1402. The body 1402 can include a proximal end 1404 and a distal end 1406. Further, the distal end 1406 of the body 1402 can have a concave tip 1408. In a particular embodiment, the implant pushing device 1400 can be fitted around the stem 1304 that extends from the body 1302 of the implant 1300.

FIG. 13 through FIG. 16 also show an implant pulling device 1500. The implant pulling device 1500 includes a generally U-shaped body 1502. The body 1502 can include a first end 1504 and a second end 1506. As illustrated, the first end 1504 can form a first hook 1508. Also, the second end 1506 can form a second hook 1510. The hooks 1508, 1510 can engage the eyelets 1308, 1310 attached to the end 1306 of the stem 1304 that extends from the body 1302 of the implant 1300.

Figure 15:
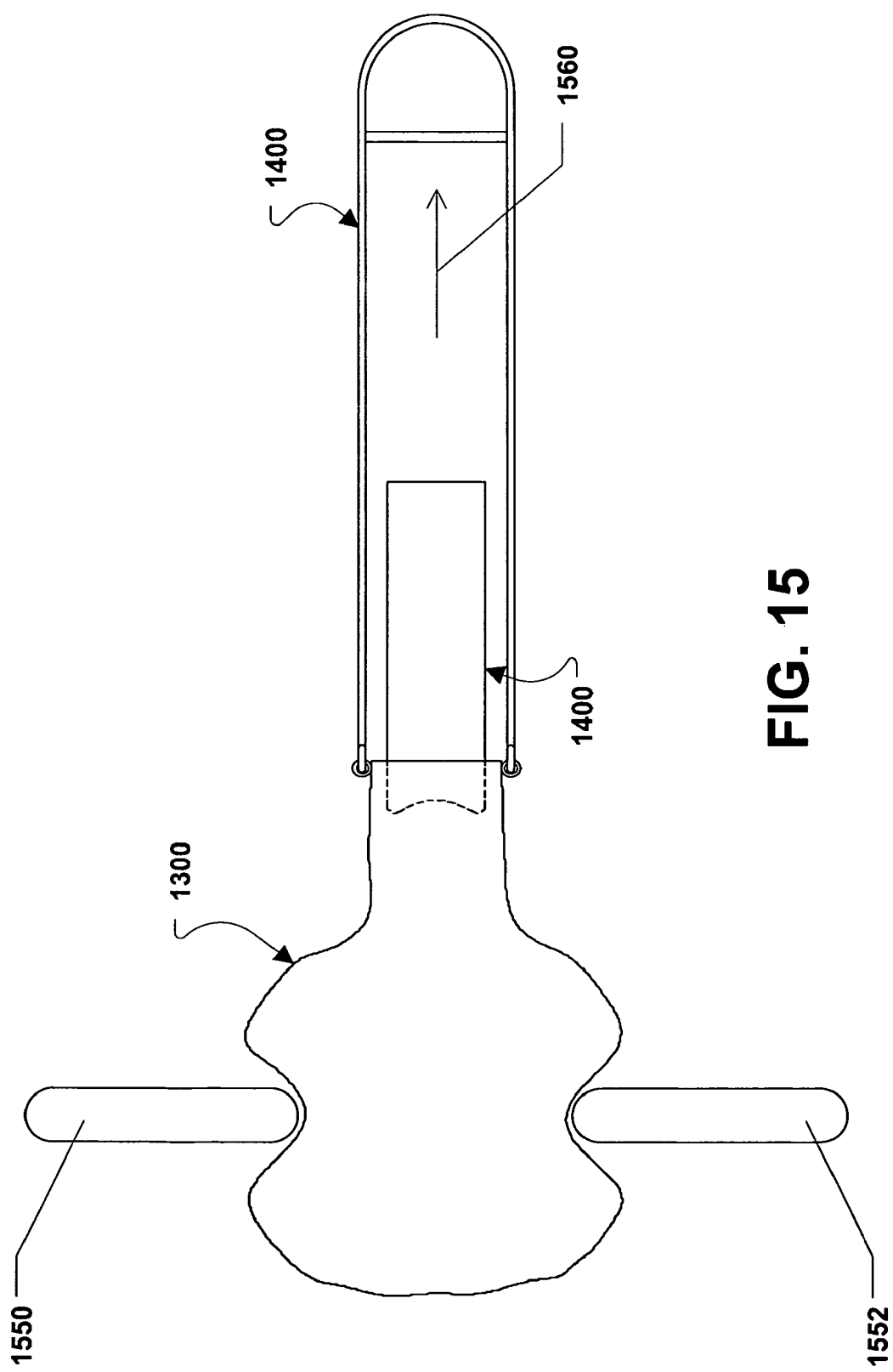
FIG. 15 is a view of the third implant in a molded, relaxed configuration between adjacent spinous processes.
Figure 16:
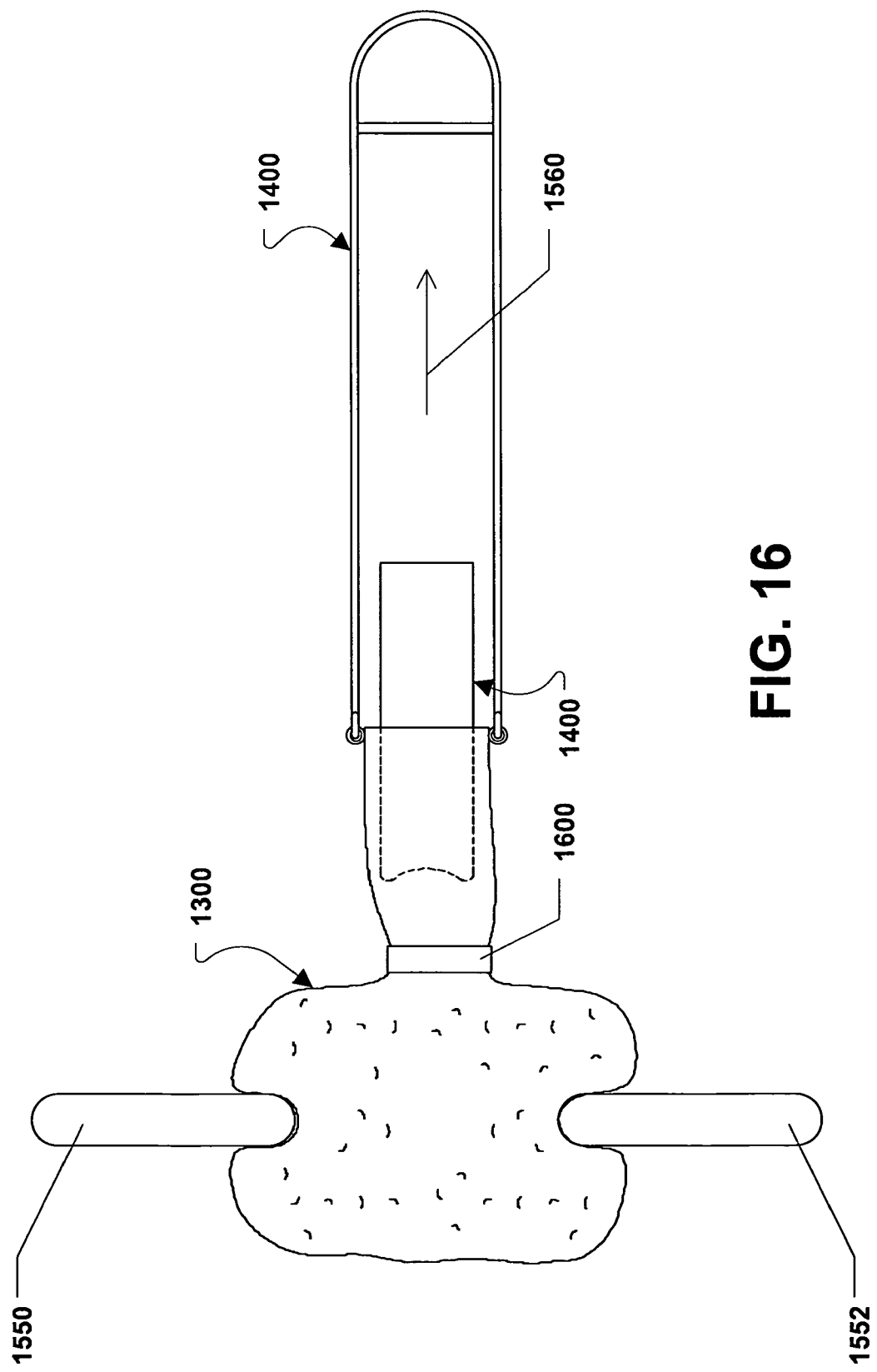
FIG. 16 is a view of the third implant in a molded, compressed configuration between adjacent spinous processes.
Figure 17:
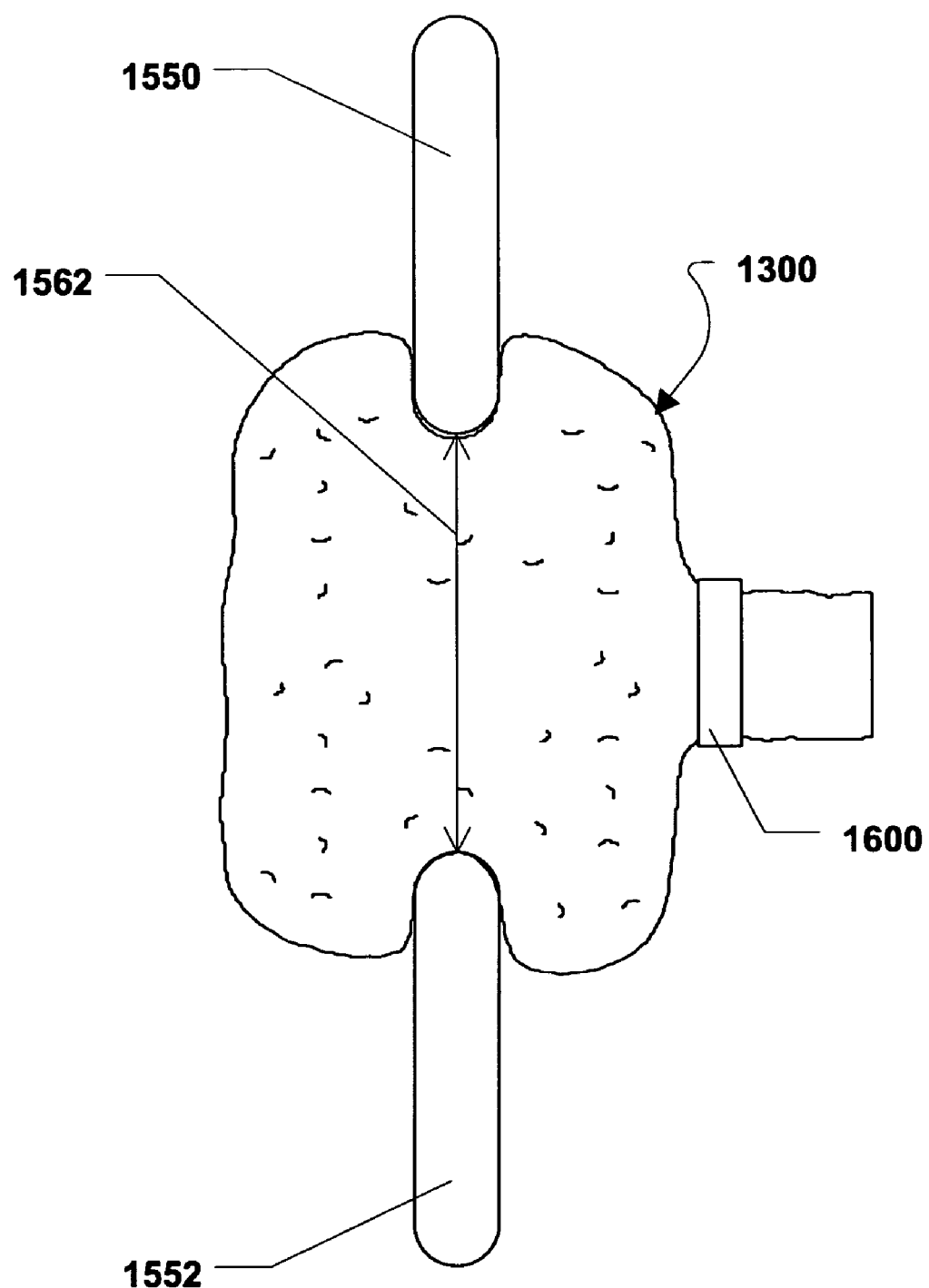
FIG. 17 is another view of the third implant in a molded, compressed configuration between adjacent spinous processes.

As shown in FIG. 15 through FIG. 17, the implant 1300 can be installed between adjacent bones or groups of bones such as, for example, a superior spinous process 1550 and an inferior spinous process 1552. Further, the implant 1300 can be moved from an unmolded, relaxed configuration, shown in FIG. 13 and FIG. 14, to a molded, relaxed configuration, shown in FIG. 15. In a particular embodiment, the implant 1300 can be manually moved to the molded, relaxed configuration. For example, the implant can be moved to a shape that closely resembles a final shape desired by the user, e.g., a surgeon.

After the implant 1300 is moved to the molded, relaxed configuration, the implant pushing device 1400 can be inserted within the stem 1304 of the implant 1300. Further, the implant pulling device 1500 can be hooked to the stem 1304 of the implant 1300. Thereafter, the implant pulling device 1500 can be moved relative to the implant pushing device 1400, as indicated by arrow 1560, in order to stretch the body 1302 of the implant 1300 around the pellets 1312. The body 1302 of the implant can include a port (not shown) or a valve (not shown) that can be configured to allow air to pass through the body 1302 as the body 1302 is stretched around the pellets 1312. Alternatively, the body 1302 can be porous and the porosity of the body 1302 can allow air to pass through the body 1302 as the body 1302 is stretched around the pellets 1312.

After the body 1302 is stretched, as indicated in FIG. 16, a band 1600 can be placed around the stem 1304 of the body 1302 in order to seal the body 1302 and prevent the pellets 1312 from being expelled from within the body 1302. The elasticity of the body 1302 can compress the pellets 1312 and cause the pellets 1312 within the body 1302 to be close-packed.

Accordingly, the implant 1300 can be moved from the molded, relaxed configuration to a molded, compressed configuration. In the molded, compressed configuration, the pellets 1312 within the body 1302 can form a relatively rigid construct that can support the adjacent spinous processes 1550, 1552 and substantially prevent a distance 1562 there between from decreasing—other than slight temporary decreases due to the elasticity of the pellets 1312 within the implant 1300. After the implant 1300 is moved to the molded, compressed configuration, the vacuum line (not shown) can be removed.

In the unmolded, relaxed configuration the pellets 1312 are loose-packed and the body 1302 does not conform to a bone, e.g., a spinous process. In the molded, relaxed configuration, the pellets 1312 remain loose-packed, but the body 1302 at least partially conforms to a bone. Further, in the molded, compressed configuration, the pellets 1312 are close-packed and the body 1302 at least partially conforms to a bone. In an exemplary embodiment, the body can contain a curable material which, when cured, can substantially maintain the pellets in the molded configuration. The curable material can be chosen from art-recognized materials that can be cured in vivo, such as a material that can be cured in situ, such as a moisture curable material. In a certain embodiment, the curable material can comprise a silicone material In a particular embodiment, in the unmolded, relaxed configuration a ratio of a volume of pellets 1312 to an interior volume of the body 1302 can be less than or equal to 0.9. Further, in the unmolded, relaxed configuration a ratio of a volume of pellets 1312 to an interior volume of the body 1302 can be less than or equal to 0.75. In the molded, compressed configuration a ratio of a volume of pellets 1312 to an interior volume of the body 1302 can be greater than or equal to 0.9. Moreover, in the molded, compressed configuration a ratio of a volume of pellets 1312 to an interior volume of the body 1302 can be greater than or equal to 0.95

In another embodiment, a distractor can be used to increase the distance 1562 between the superior spinous process 1550 and the inferior spinous process 1552 and the implant 1300 can be placed within the distracted superior spinous process 1550 and the inferior spinous process 1552. After the implant 1300 is moved to the molded, compressed configuration, as described herein, the distractor can be removed and the implant 1300 can support the superior spinous process 1550 and the inferior spinous process 1552 and substantially prevent the distance 1562 between the superior spinous process 1550 and the inferior spinous process 1552 from returning to a pre-distraction value.

Description of a Method of Treating a Spine

Figure 18:
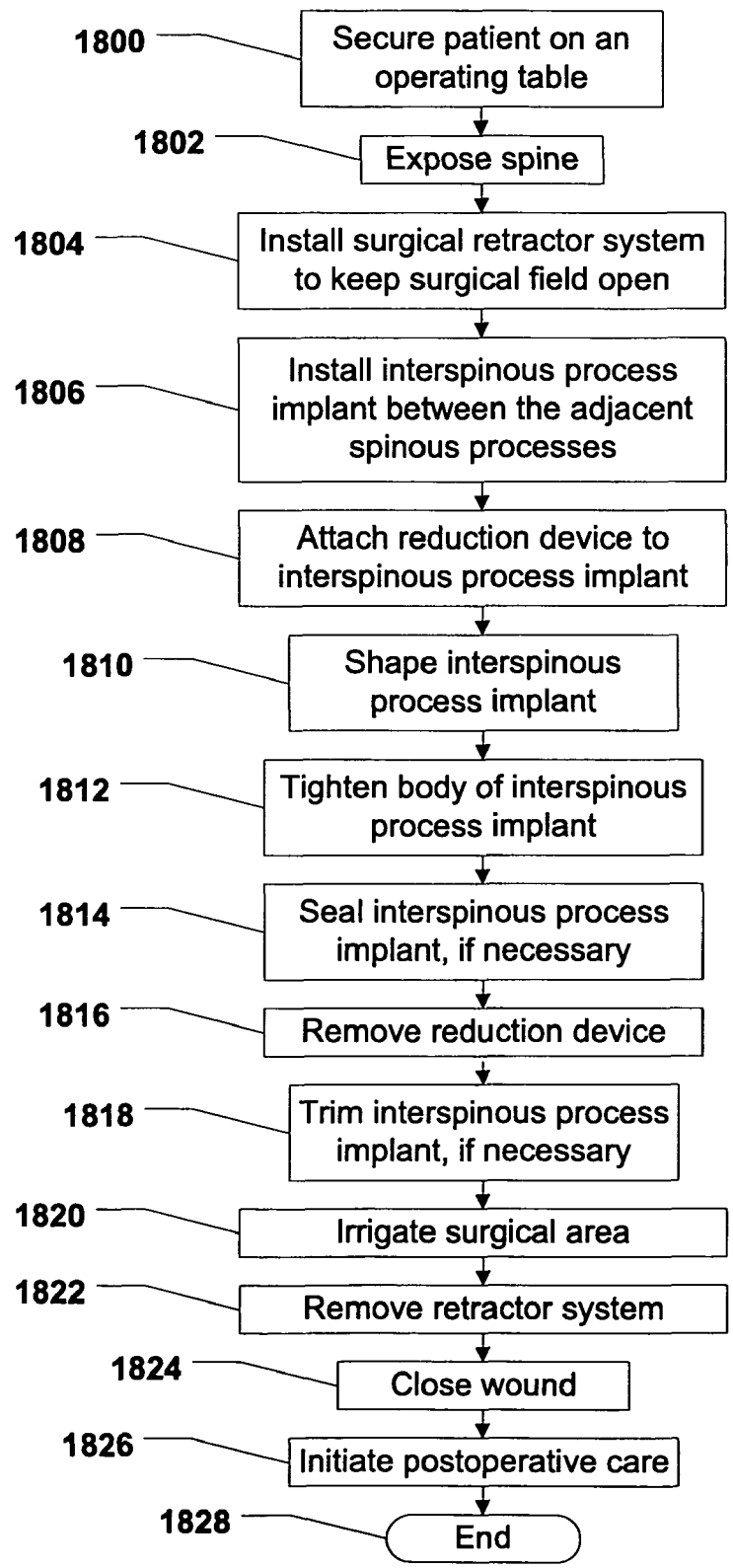
FIG. 18 is a flow chart illustrating a method of treating a spine.

Referring to FIG. 18, a method of treating a spine is shown and commences at block 1800. At block 1800, a patient can be secured on an operating table. Depending on the surgical approach to be used, the patient can be secured in a prone position for a posterior approach, a supine position for an anterior approach, a lateral decubitus position for a lateral approach, or another position well known in the art. At block 1802, the spine can be exposed in order to expose adjacent spinous processes. Further, at block 1804, a surgical retractor system can be installed to keep surgical field open.

Moving to block 1806, an implant can be installed between the adjacent spinous processes. In a particular embodiment, the implant can be an implant according to one or more of the embodiments described herein. At block 1808, a compression device can be connected to the implant. In a particular embodiment, the compression device can be a vacuum system, an implant pushing device, an implant pulling device, or a combination thereof.

Proceeding to block 1810, the implant can be moved to a molded, relaxed configuration in which the implant approximates a final desired shape. In a particular embodiment, the implant can be moved to the molded, relaxed configuration manually. Thereafter, at bock 1812, the implant can moved to the molded, compressed configuration. The implant can be moved to the molded, compressed configuration by evacuating the air within the implant or by stretching the body of the implant so the body compresses a plurality of pellets therein.

At block 1814, the implant can be sealed, if necessary. For example, if the implant does not include a valve, the implant can be sealed using a band or other similar device. At block 1816, the compression device can be removed from the implant.

Continuing to block 1818, the implant can be trimmed, if necessary. For example, if the body of the implant is stretched and sealed with a band, a portion of a stem, around which the band is installed, may be removed. Thereafter, at block 1820, the surgical area can be irrigated. At block 1822, the retractor system can be removed. Further, at block 1824, the surgical wound can be closed. The surgical wound can be closed by simply allowing the patient's skin to close due to the elasticity of the skin. Alternatively, the surgical wound can be closed using sutures, surgical staples, or any other suitable surgical technique well known in the art. At block 1826, postoperative care can be initiated. The method can end at state 1828.

In a particular embodiment, the spinous processes can be distracted prior to inserting the implant. After the implant is moved to the molded, compressed configuration, the distractor can be removed and the implant can support the superior spinous process and the inferior spinous process and substantially prevent a distance between the superior spinous process and the inferior spinous process from returning to a pre-distraction value.

Conclusion

With the configuration of structure described above, the implant provides a device that can be used to treat a spine and substantially alleviate or minimize one or more symptoms associated with disc degeneration, facet joint degeneration, or a combination thereof. For example, the implant can installed between adjacent spinous processes, molded, and compressed in order to support the spinous processes and maintain them at or near a predetermined distance there between. Although the present Figures show use of the present implant as an interspinous process brace, the implant can be used in other applications, such as a nucleus implant, an intervertebral disc prosthesis or the like.

The above-disclosed subject matter is to be considered illustrative, and not restrictive, and the appended claims are intended to cover all such modifications, enhancements, and other embodiments that fall within the true spirit and scope of the present invention. Thus, to the maximum extent allowed by law, the scope of the present invention is to be determined by the broadest permissible interpretation of the following claims and their equivalents, and shall not be restricted or limited by the foregoing detailed description.

What is claimed is:

1. An interspinous device for insertion between upper and lower spinous processes, comprising:
    a flexible container having a plurality of pellets disposed therein, the container having first and second states;
    in the first state the container contains the pellets in a looser packed configuration with a corresponding first amount of interstitial fluid;
    in the second state the container binds the pellets in a tighter packed configuration with a corresponding second amount of interstitial fluid, the second amount of interstitial fluid being less than the first amount of interstitial fluid; and
    the first and second states having an equal amount of pellets disposed in the container.

2. The interspinous device of claim 1 further comprising:
    a stem extending outwardly from the flexible container;
    a pushing device and a pulling device, each configured to be engaged with the stem; and
    wherein the pushing device and pulling device are moveable relative to each other to cause the container to change from the first state to the second state.

3. The interspinous device of claim 2 wherein the pushing device is at least partially inserted within the stem.

4. The interspinous device of claim 2 wherein the pushing device is mounted to an external portion of the stem.

5. The interspinous device of claim 2 wherein the container comprises a port for removing at least a portion of the interstitial volume of fluid.

6. The interspinous device of claim 2 wherein the container comprises pores for removing at least a portion of the interstitial volume of fluid.

7. The interspinous device of claim 1 wherein the second amount of interstitial fluid is a curable fluid.

8. The interspinous device of claim 1 wherein when device is disposed between the upper and lower spinous processes and the container is in the second state, the container includes first and second upper arms and first and second lower arms, the upper arms forming a portion of an upper saddle, and the lower arms forming a portion of a lower saddle.

* * * * *